United States Patent
Weinberg

(10) Patent No.: US 6,312,700 B1
(45) Date of Patent: Nov. 6, 2001

(54) METHOD FOR ENHANCING AN ANTIGEN SPECIFIC IMMUNE RESPONSE WITH OX-40L

(76) Inventor: Andrew D. Weinberg, 3266 SW. Fairmount Blvd., Portland, OR (US) 97201

( * ) Notice: Subject to any disclaimer, the term of this patent is extended or adjusted under 35 U.S.C. 154(b) by 0 days.

(21) Appl. No.: 09/255,363

(22) Filed: Feb. 23, 1999

Related U.S. Application Data

(60) Provisional application No. 60/075,801, filed on Feb. 24, 1998.

(51) Int. Cl.[7] .......................... A61K 39/00; A61K 39/02; A61K 39/12; A61K 39/18; A61K 45/00
(52) U.S. Cl. .................................. 424/278.1; 424/134.1; 424/192.1; 424/204.1; 424/234.1; 424/277.1; 530/350; 530/351; 530/387.1; 530/387.3
(58) Field of Search .................................... 530/350, 351, 530/387.1, 387.3; 424/85.1, 130.1, 133.1, 134.1, 184.1, 192.1, 278.1, 204.1, 234.1, 277.1; 514/885

(56) References Cited

U.S. PATENT DOCUMENTS

| | | |
|---|---|---|
| 4,590,071 | 5/1986 | Scannon et al. . |
| 4,664,911 | 5/1987 | Uhr et al. . |
| 4,681,760 | 7/1987 | Fathman . |
| 4,731,244 | 3/1988 | Talle et al. . |
| 4,867,973 | 9/1989 | Goers et al. . |
| 5,045,451 | 9/1991 | Uhr et al. . |
| 5,057,313 | 10/1991 | Shih et al. . |
| 5,057,598 | 10/1991 | Pollack et al. . |
| 5,091,177 | 2/1992 | Hellström et al. . |
| 5,167,956 | 12/1992 | Neville et al. . |
| 5,329,028 | 7/1994 | Ashkenazi et al. . |
| 5,376,367 | 12/1994 | Williams . |
| 5,457,035 | 10/1995 | Baum et al. . |
| 5,578,707 | 11/1996 | Novick et al. . |
| 5,821,332 | 10/1998 | Godfrey et al. . |

FOREIGN PATENT DOCUMENTS

| | | |
|---|---|---|
| WO 89/06967 | 10/1989 | (WO) . |
| WO 95/12673 | 5/1995 | (WO) . |
| WO 95/21915 | 8/1995 | (WO) . |

OTHER PUBLICATIONS

Aversa et al., Activation panel antigen expression on PBL activated by PHA or in MLR, Leukocyte Typing IV. White Cell Differentiation Antigens, pp. 498–501 (1989).

Baum et al., Molecular characterization of murine and human OX40/OX40 ligand systems: identification of a human OX40 ligand as the HTLV–1–regulated protein gp34, The EMBO Journal, 13:17:3992–4001 (1994).

Dunlap et al., Expression of activation antigens on HTLV–I and HTLV–II cell lines, Leukocyte Typing IV. White Cell Differentiation Antigens, pp. 487–488 (1989).

Flanagan et al., The kit Ligand: A Cell Surface Molecule Altered in Steel Mutant Fibroblasts, Cell 63:185–194 (1990).

Fraser et al., Ligand–induced association between the T–cell antigen receptor and two glycoproteins, Proc. Natl. Acad. Sci. 86:7133–7137 (1989).

Godfrey et al., A New Member of the FAS/TNFr Superfamily Expessed Selectively on Activated CD4+T–cells, Journal of Cellular Biochemistry, Supplement 0:18D, Abstract V370 (1994).

Godfrey et al., Identification of a Human OX–40 Ligand, a Costimulator of CD4+T Cells with Homology, J. Exp. Med. 180:757–762 (1994).

Godfrey et al., Molecular Cloning of a cDNA Encoding the Hman Homolog of the Rat OX–40 Antigen, Tissue Antigens 42:4:253 — AA057 (1993).

Hamilton–Dutoit et al., An immunohistological analysis of the mAb in the activation antigen panel, Leukocyte Typing IV. White Cell Differentiation Antigens, pp. 475–476 (1989).

Holoshitz et al., Arthritis Induced in Rats by Cloned T Lymphocytes Responsive to Mycobacteria but Not to Collagen Type II, J. Clin. Invest. 73:211–215 (1984).

Kennedy et al., Analysis of Cytokine mRNA Expression in the Central Nervous System of Mice with Experimental Autoimmune Encephalomyelitis Reveals that IL–10 mRNA Expression Correlates with Recovery, J. Immun. 149:2496–2505 (1992).

Khoury et al., Oral Tolerance to Myelin Basic Protein and Natural Recovery from Experimental Autoimmune Encephalomyelitis Are Associated with Downregulation of Inflammatory Cytokines and Differential Upregulation of Transforming Growth Factor β, Interleukin 4, and Prostaglandin E Expression in the Brain, J. Exp. Med. 176:1355–1364 (1992).

King et al., Tonsillar dendritic–cell–induced T–lymphocyte proliferation: analysis of molecular mechanisms using the activation panel of mAb, Leukocyte Typing IV. White Cell Differentiation Antigens, pp. 503–505 (1989).

Latza et al., The human OX40 homolog: cDNA structure, expession and chromosomal assignment of the ACT35 antigen, Eur. J. Immunol. 24:677–683 (1994).

(List continued on next page.)

*Primary Examiner*—Phillip Gambel
*Assistant Examiner*—Jessica H. Roark
(74) *Attorney, Agent, or Firm*—Klarquist Sparkman, LLP

(57) ABSTRACT

Compositions and methods for enhancing the immune response of a mammal to an antigen by engaging the OX-40 receptor on the surface of T-cells are disclosed, comprising administering to the mammal a composition comprising a purified OX-40 receptor binding agent and a pharmaceutically acceptable carrier, wherein said composition is administered to the mammal such that the OX-40 receptor binding agent is presented to T-cells of the mammal during or shortly after priming of the T-cells by the antigen. Such compositions and methods can be used in immunization and cancer treatment.

23 Claims, 14 Drawing Sheets

OTHER PUBLICATIONS

Mallett et al., A new superfamily of cell surface proteins related to the nerve growth factor receptor, Immunology Today 12:220–223 (1991).

Mallett et al., Characterization of the MRC OX40 antigen of activated CD4 positive T lymphocytes—a molecule related to nerve growth factor receptor, The EMBO Journal 9:1063–1068 (1990).

Marston, The purification of eukaryotic polypeptides synthesized in *Escherichia coli*, Biochemistry Journal 240:1–12 (1986).

Mehra et al., Efficient mapping of protein antigenic determinants, Proc. Natl. Acad. Sci. 83:7013–7017 (1986).

Miura et al., Molecular cloning and Characterization of a Novel Glycoprotein, gp34, That Is Specifically Induced by the Human T–Cell Leukemia Virus Type I Transactivator $p40^{tax}$, Molecular and Cellular Biology 11:1313–1325 (1991).

Parker at al., Fusion Proteins in Immunointervention, Trans. Proc. 24:2362–2365 (1992).

Paterson et al., Antigens of Activated Rat T Lymphocytes Including a Molecule of $50,000M_r$, Detected Only on CD4 Positive T Blasts, Mol. Immun. 24:1281–1290 (1987).

Picker et al., Control of Lumphocyte Recirculation in Man. Differential Regulation of the Peripheral Lumph Node Homing Receptor L–Selectin on T Cells during the Virgin to Memory Cell Transition, The Journal of Immunology 150:1105–1121 (1993).

Picker et al., Control of Lumphocyte Recirculation in Man. Differential Regulation of the Cutaneous Lymphocyte–Associated Antigen, a Tissue–Selective Homing Receptor for Skin–Homing T Cells, The Journal of Immunology 150:1122–1136 (1993).

Rentrop et al., Biochemical analysis of the Workshop antibodies of the Activation Section, Leukocyte Typing IV. White Cell Differentiation Antigens, pp. 473–474 (1989).

Tanaka et al., A Glycoprotein Antigen Detected with New Nomoclonal Antibodies on the Surface of Human Lymphocytes Infected with Human T–Cell Leukemia Virus Type–I (HTLV–I), Int. J. Cancer 36:549–555 (1985).

Tozawa et al., Species–Dependent antigenicity of the 34–kDa Glycoprotein Found on the Membrane of Various Primate Lymphocytes Transformed by Human T–cell Leukemia Virus Type–I (HTLV–I) and Simian T–cell Leukemia Virus (STLV–I), Int. J. Cancer 41:231–238 (1988).

Vilella et al., Sequential appearance of the activation antigens, Leukocyte Typing IV. White Cell Differentiation Antigens, pp. 495–497 (1989).

Vitetta et al., Phase I Immunotoxin Trial in Patients with B–Cell Lymphoma, Cancer Res. 51:4052–4058 (1991).

Waldmann, Monoclonal Antibodies in Diagnosis and Therapy, Science 252:1657–1662 (1991).

Waugh et al., Staining of normal or rejecting kidney using the activation panel, Leukocyte Typing IV. White Cell Differentiation Antigens, pp. 485–486 (1989).

Gramaglia et al., Ox–40 Ligand: A Potent Costimulatory Molecule for Sustaining Primary CD4 T Cell Responses, J. of Immunology 161:6510–6517 (1998).

Morris et al., Susscessful Transfexction of the Ox–40 Ligand in Murine and Human Tumor Cell Lines, Proc. Am. Assoc. Cancer Res 38:401 (1997).

Morris et al., Breast Cancer Immunity in Mice Treated with the Ox–40 Ligand, Proc. Am. Assoc. Cancer. Res. 39:531 (1998).

Vetto et al., Presence of the T–Cell Activation Marker Ox–40 on Tumor Infiltrating Lymphocytes and Draining Lymph Node Cells from Patients with Melanoma and Head and Neck Cancers, American J. of Surgery 174:258–265 (1997).

Weinberg et al., Antibodies to Ox–40 (CD134) Can Identify and Eliminate Autoreactive T Cells: Implications for Human Autoimmune Disease, Molecular Medicine Today 2:76–83 (1998).

Weinberg et al., Ox–40: Life Beyond the Effector T Cell Stage, Immunology 10:471–480 (1998).

Weinberg et al., *J. Immunol.*, 148:2109–2117, 1992.

Young et al., *Pro. Natl. Acad. Sci.*, 80:1194–1198, 1983.

Days After Tumor Injection

Days Post F10 Injection

US 6,312,700 B1

METHOD FOR ENHANCING AN ANTIGEN SPECIFIC IMMUNE RESPONSE WITH OX-40L

PRIORITY CLAIM

This patent application claims priority from U.S. Provisional Application, Ser. No. 60/075,801, filed on Feb. 24, 1998, which is herein incorporated by reference.

FIELD OF THE INVENTION

This invention relates to methods and compositions for generating enhanced immune responses in animals, particularly in human and non-human mammals. The invention also relates to production of compositions and materials for use in the methods, for example to related vaccines, cells, plasmids, viral and other vectors, and preparations derived therefrom. Other aspects of the invention will be apparent from the following description.

BACKGROUND OF THE INVENTION

It is known that many receptor-ligand interactions are involved in the induction, establishment and modulation of immune responses directed against antigens. At least two signals are necessary to activate a CD4 or CD8 T-cell response to antigen (Lenschow et al., 1996). The first signal is delivered through the T-cell receptor (TCR) by an antigen (typically a peptide) bound to a major histocompatibility (MHC) class I or II molecule present on the surface of an antigen presenting cell (APC). The second signal involves the binding of a ligand present on the surface of the APC to a second receptor molecule on the surface of the T-cell. This second signal is termed co-stimulation, and the APC ligand is often referred to as a co-stimulatory molecule. The best characterized second signal is delivered via an interaction between the CD28 receptor on the T-cell, and its ligands B7.1 or B7.2 on the APC, although a number of other examples of receptor/co-stimulatory molecule interactions have been described.

In combination, the two signals activate the T-cell, which in turn secretes cytokines and proliferates. In the case of CD4 T-cells, the activated cells (designated CD4$^+$) produce cytokines, including IL-2 and IFN$\gamma$, which activate killer (CD8$^+$) T-cells at the site of inflammation. Once CD4 T-cells are activated, another receptor, CTLA-4 is expressed, which is homologous to CD28 and binds B7 molecules with a higher affinity than CD28. The B7/CTLA-4 interaction inhibits the activation signal of CD28 and delivers a negative signal that may down-regulate T-cell responses (Krummel et al., 1996; Walunas et al., 1996). This down-regulation mechanism may serve to prevent excessive immune system responses, for example by decreasing the amount of cytokines produced during an inflammatory event. Concurrently, however, it may also down-regulate the number of T-cells that go on to become "memory cells". Reducing the number of memory cells means that fewer such cells will be available to respond to the same antigen the next time it is encountered. However, there are a number of situations where it would be advantageous to maintain, rather than down-regulate, an active T-cell response. Cancer patients, for example, would benefit from maintaining an active T-cell response against tumor cells. The concept of vaccination requires that a population of memory T-cells which recognized the administered antigen be maintained.

Another receptor/ligand combination that has been proposed to play a role in co-stimulation of CD4 T-cells is the OX-40 receptor/OX-40 ligand pairing. While the CD28 receptor is present on the surface of many sub-classes of T-cells (irrespective of whether they are activated or not), the OX-40 receptor ("OX-40") (Paterson et al. 1987; Calderhead et al., 1993) has been shown to be present only on antigen activated CD4$^+$ T-cells in vivo (Weinberg et al., 1994; 1996). Thus, it has been shown that OX-40 is present on activated CD4$^+$ T-cells that recognize autoantigen at the site of inflammation in autoimmune disease, but not in the peripheral blood system (Weinberg et al, 1994; 1996). OX-40 has also been shown to be present on the surface a percentage of CD4$^+$ T-cells isolated from tumor infiltrating lymphocytes and draining lymph node cells removed from patients with squamous cell tumors of the head and neck and melanomas (Vetto et al., 1997). The OX-40 ligand, a member of the tumor necrosis factor (TNF) superfamily, has been shown to co-stimulate T-cells which have been activated with an anti-CD-3 antibody (i.e., in a nonantigen-specific manner) (Godfrey et al., 1994). Beyond its general co-stimulatory function however, the biological role of the OX-40 receptor/OX-40 ligand interaction in the immune response pathway is, to date, unknown.

SUMMARY OF THE INVENTION

This invention provides in certain of its aspects compositions and methods which can be used to enhance and maintain the immune response of a mammal towards a chosen antigen. While prior procedures have attempted to boost the immune response generally, compositions and methods disclosed herein are specifically targeted to T-cells which have recently been activated in response to a particular antigen (so-called "memory cells") or T-cells which are in the process of such priming. In particular, the effects of the methods disclosed herein are believed to include increasing the number of memory T-cells, thereby enhancing the response of the immune system to a specific (chosen) antigen.

Underlying the invention are findings (1) that engagement of the OX-40 receptor on CD4$^+$ T-cells especially for example during, or shortly after, priming of such cells by antigen, can result in an increased response of the CD4$^+$ T-cells to that antigen and (2) that the elevated response to that antigen can be maintained for a period of time substantially longer than in the absence of such an engagement. As a result, increasing the immune response by providing molecules which engage the OX-40 receptor, e.g. during T-cell priming, can markedly increase the resistance of an animal to disease, by boosting T-cell recognition of antigens presented by infectious agents, such as bacteria and viruses, as well as tumor cells.

Accordingly, the present invention provides among other things the use of an OX-40 receptor binding agent, or of a nucleic acid encoding an OX-40 receptor binding agent, in the manufacture of a pharmaceutical composition for enhancing immune response against an antigen in a mammal, which is either a tumour antigen, or an antigen for which the composition is administered so as to present the OX-40 receptor binding agent to T-cells of the mammal during or shortly after priming of the T-cells by the antigen.

The OX-40 receptor binding agent can be selected from OX-40L, anti-OX-40 antibodies (e.g. a monoclonal antibody such as a humanized monoclonal antibody), and immunologically effective portions of anti-OX-40 antibodies.

The antigen can be selected from viral antigens, bacterial antigens and tumor antigens.

Also according to the invention, a purified OX-40 receptor binding agent and a pharmaceutically acceptable carrier can be used in the manufacture of a pharmaceutical composition for enhancing the immune response of a mammal to an antigen by administering the composition to the mammal to present the OX-40 receptor binding agent to T-cells of the mammal during or shortly after priming of the T-cells by the antigen, e.g. about 3–7 days after administration of the antigen.

The technique can be applied to enhancing the immune response of a mammal to a tumour cell in the mammal.

One form in which the invention can be carried out is by the use of a nucleic acid encoding an OX-40 receptor binding agent that is localised on the surface of a cell (e.g. by possessing a suitable transmembrane sequence), in the manufacture of a composition for introducing the nucleic acid into a cell and enhancing the immunogenicity of the cell, e.g. a tumor cell.

The nucleic acid can if desired further encode a second protein, e.g. one selected from major histocompatibility complex proteins, cytokines, interferons and immune-system co-stimulatory molecules.

The nucleic acid encoding the OX-40 receptor binding agent can be made part of a viral or plasmid vector, e.g. a viral vector based on an adenovirus, retrovirus or herpesvirus. The viral vector can be an attenuated or disabled virus.

According to a further aspect of the invention a nucleic acid which encodes an OX-40 receptor binding agent that is localised on the surface of a cell, along with tumor cells from a mammal, can be used in the manufacture of a pharmaceutical composition for stimulating the immune response of a mammal to a tumor in the mammal by (a) removing tumor cells from the mammal; (b) attenuating the removed tumor cells; (c) introducing the nucleic acid into the attenuated tumor cells; and (d) administering the thus-treated attenuated tumor cells containing the nucleic acid molecule to the mammal. The OX-40 receptor binding agent in this aspect can be OX-40L. The tumor cells can be attenuated prior to or after introducing the nucleic acid molecule.

In an alternative manner of carrying out the invention, a nucleic acid which encodes an OX-40 receptor binding agent that is localised on the surface of a cell can be used, along with T-cells from a mammal, in the manufacture of a pharmaceutical composition for enhancing the immune response of a mammal to an antigen, by removing T-cells from the mammal, incubating the removed T-cells ex vivo with an OX-40 receptor binding agent, and returning the thus-treated T-cells to the mammal. Again, the mammal may have a tumor, and the antigen can be a tumor antigen.

More generally, an OX-40 receptor binding agent or a nucleic acid encoding an OX-40 receptor binding agent can be used in the manufacture of a pharmaceutical for enhancing immune response against a tumor in a mammal by increasing the amount of OX-40 receptor binding agent at the tumor site.

The invention in other aspects also provides inter alia tumor cells that have been transformed with a nucleic acid encoding an OX-40 receptor binding agent that is localised on the surface of the cell, and compositions comprising cell membranes isolated from such cells.

The invention further provides compositions with the features and for the purposes set forth herein, and methods of making and using those compositions.

In one example of the invention, made for comparison with administration of certain tumor cells to animals which alone result in 100% lethality, administration of molecules which engage the OX-40 receptor along with the tumor cells protected the animals from the tumor cells.

Without intent to be bound by theory, one possible explanation of the mechanism underlying this discovery is depicted in FIG. 1 of the accompanying drawings. FIG. 1 schematically illustrates the role of CD4 T-cells in the immune system. Naive T-cells (i.e., those not previously exposed to antigen) in the spleen or lymph nodes differentiate into activated cells ("effectors") in response to antigen. As discussed above, the activation requires presentation of antigen in the context of an MHC molecule, together with a co-stimulatory molecule. Co-stimulatory molecules characterized to date, such as the B7 molecule, are believed to act at the naive/effector cell transition. After activation, a substantial subset of these effector cells is proposed to produce cytokines and, through a feed-back mechanism which may involve certain T-cell receptor/ligand interactions (e.g., CTLA-4/B7), subsequently undergoes programmed cell death. The remaining subset of T-cells expands and goes on to become memory cells, ready to respond to future exposures to the antigen. It is believed that co-stimulation of T-cells by engagement of the OX-40 receptor during this period can increase effector T-cell function and also increase the proportion of antigen-specific activated $CD4^+$ T-cells which remain after the initial antigen exposure and which eventually adopt a memory phenotype. Thus, it is proposed that, in contrast to conventional co-stimulatory molecules which act at the naive/effector cell transition, OX-40 ligands act at the effector/memory cell transition. Therefore, the methods of the present invention, which involve engagement of the OX-40 receptor, serve to increase the proportion of effector cells which go on to become memory cells. By increasing this population of cells, the present and future ability of the immune system to respond to that specific antigen is enhanced and this enhanced response capability is maintained for a significantly longer period of time. In contrast, previously described methods of enhancing the immune response by providing co-stimulatory molecules make use of co-stimulatory molecules, such as B7, which act at the naive/effector cell transition (see, for example, European Patent Application EP 0 733 373 (Bristol Myers Squibb: L Chen et al: Compositions and methods for increasing the immunogenicity of tumor cells by administration of B7 and CD2-transfected cells)). It is believed that enhancement of the population of antigen-specific memory cells has not heretofore been disclosed, but rather enhancement of an initial immune response. Methods for enhancing the immune response as described here are believed to be able to produce good enhancement of the immune response by boosting the population of antigen-specific memory T-cells.

It is emphasized that this is only one possible explanation for the invention disclosed and claimed herein; regardless of the actual mechanism, the administration of molecules which engage the OX-40 receptor during antigen activation is provided hereby and can confer significant immunological benefit.

Molecules which can engage the OX-40 receptor are herein referred to as OX-40 receptor binding agents.

Thus, in one aspect the present invention provides a method for inducing or enhancing an immune response mediated by $CD4^+$ T-cells against an antigen, which comprises delivering to $CD4^+$ T-cells during, or shortly after, antigen priming has occurred in vivo, an OX-40 receptor binding agent. Compositions for use in such a method which comprise an OX-40 receptor binding agent and a suitable carrier are also provided.

OX-40 receptor binding agents useful in the present invention include the OX-40 ligand, functional domains of the OX-40 ligand, such as the extracellular domain, either alone or conjugated to other peptide domains, e.g. as fusion proteins, and antibodies with anti-OX-40 receptor specificity.

Such OX-40 receptor binding agents can be used to induce or enhance a CD4$^+$ T-cell mediated immune response against a wide variety of antigens, including viral antigens, bacterial antigens and tumor antigens. In one aspect of the invention, OX-40 receptor binding agents can be used to enhance the immune response of an animal to an antigen.

Thus, the present invention further provides a method of enhancing the immune response of an animal to an antigen, comprising administering to the animal a composition comprising a purified OX-40 receptor binding agent and a pharmaceutically acceptable carrier, wherein said composition is administered to the animal such that the OX-40 receptor binding agent is presented to T-cells of the mammal during or shortly after priming of the T-cells by the antigen. The process of T-cell priming by an antigen in mammals is considered to take place within about 3–7 days following delivery of antigen. "Shortly after priming" thus generally refers to a time period of about 3–10 days following administration of antigen.

According to a further aspect of the present invention, the OX-40 receptor binding agent can be administered to a mammal for example up to approximately 10 days after, more typically about a week after, and preferably about 3–7 days after, administration of an antigen preparation in order to enhance the CD4$^+$ T-cell mediated immune response of the mammal against the administered antigen. The exact timing is believed often not to be critical.

The present invention also provides methods for enhancing the immune response of a mammal to a tumor. In one such method, the immune response of a mammal to a tumor is stimulated by administering to the mammal a therapeutically effective dose of a purified OX-40 receptor binding agent.

Vaccine compositions encompassed by the invention include one or more antigens and a therapeutically effective amount of an OX-40 receptor binding agent. As noted above, the antigen may be selected from the group consisting of tumor antigens, bacterial antigens and viral antigens. Where the vaccine includes a viral antigen and where the viral antigen is delivered by means of an attenuated or replication-defective virus, the OX-40 receptor binding agent may be provided by means of a nucleic acid molecule encoding the agent inserted into the viral genome, such that it is expressed in the cells of the mammal to which the vaccine is delivered. Where the vaccine includes a bacterial antigen delivered by means of an attenuated bacterium or a preparation of bacterial antigens, the OX-40 receptor binding agent may be provided by means of a nucleic acid molecule encoding the agent, which nucleic acid molecule is contained and expressed within the bacterial cell. Similarly, where the vaccine includes a tumor antigen preparation, such as tumor cell membranes, the OX-40 receptor binding agent may be provided by means of a nucleic acid molecule encoding the agent, which nucleic acid molecule is expressed within the tumor cell prior to disruption of the cell for vaccine preparation. The antigen and a material providing an OX40 receptor binding agent can be delivered to the animal either separately or together: the period of time referred to as shortly after priming refers to physiologically effective contact, which may occur after physical administration especially where what is administered is a composition that indirectly provides the OX40 receptor binding agent in vivo, e.g. the nucleic acid mentioned above.

A further aspect of the invention is the provision or enhancement of OX-40 receptor binding agent expression in cell, such as an antigen presenting cell (APC), e.g., a tumor cell. Expression of OX-40 receptor binding agent in an APC may be achieved by delivering into the cell a vector carrying a nucleic acid sequence encoding the agent, wherein expression of the nucleic acid sequence results in levels of expression of the agent that are higher than those in a comparable cell lacking the vector. Suitable vectors for delivering and expressing the OX-40 receptor binding agent are well known in the art and include plasmid vectors and viral vectors, such as adenovirus, herpesvirus and retrovirus vectors. In certain embodiments, the vector may carry one or more additional nucleic acid sequences which encode antigens against which an immune response is desired. Thus, one aspect of the invention is a method for enhancing the immunogenicity of a cell, the method comprising introducing into the cell a nucleic acid molecule encoding an OX-40 receptor binding agent, such that the OX-40 receptor binding agent is expressed on the surface of the cell.

In another aspect of the invention, the APC may be a tumor cell removed from a mammalian subject. In this respect, the invention is useful for enhancing a mammal's immune response against tumor cells present in its body. In one embodiment of the invention, tumor cells are removed from a mammal. A vector expressing the OX-40 receptor binding agent is then introduced into the removed cells, which are then returned to the mammal. Preferably, the tumor cells are attenuated prior to re-introduction to the patient; mechanisms for attenuating tumor cells are well known and include, for example, irradiation. The result of this procedure is that the re-introduced attenuated tumor cells simultaneously present both tumor antigens and the OX-40 receptor binding agent to CD4 T-cells, resulting in an elevated CD4$^+$ T-cell mediated immune response against tumor cells in the body of the mammal. Since certain tumor cells evade the body's immune system by down-regulating expression of antigen-presenting MHC molecules, it may be advantageous to introduce into the removed tumor cells not only a vector which expresses the OX-40 receptor binding agent, but also a vector which expresses an MHC molecule, preferably an MHC class II molecule. In certain embodiments of the invention, a single vector which expresses both the OX-40 receptor binding agent and the MHC molecule may be introduced into the tumor cells. Thus, in another aspect of the invention, a method for stimulating the immune response of a mammal to a tumor in the mammal is provided, wherein the method comprises: (a) removing tumor cells from the mammal; (b) attenuating the removed tumor cells; (c) introducing into the attenuated tumor cells a nucleic acid molecule which encodes an OX-40 receptor binding agent such that the OX-40 receptor binding agent is expressed on the surface of the attenuated tumor cells; and (d) administering a therapeutically effective dose of a preparation of the attenuated tumor cells containing the nucleic acid molecule to the mammal.

The present invention also provides novel methods of adoptive immunotherapy in which the immune response of a mammal to an antigen is enhanced by removing T-cells from the mammal, incubating the removed T-cells ex vivo with an OX-40 receptor binding agent, and returning the T-cells to the mammal. Such a method may be particularly beneficial for the treatment of cancer patients. The invention also provides a method for enhancing the immune response of an animal against a tumor, comprising increasing the amount of an OX-40 receptor binding agent at the tumor site (i.e., the area of the body including and immediately adjacent to the tumor). Increasing the amount of OX-40 receptor binding agent may be achieved by administering to the tumor site a composition selected from the group consisting of OX-40 receptor binding agents and nucleic acid molecules encoding OX-40 receptor binding agents.

The invention is further described by way of example but not with intent to limit the scope of the invention thereby, in the description, figures of the accompanying drawings, and examples set forth below.

DETAILED DESCRIPTION

1. Definitions

Figure 1:
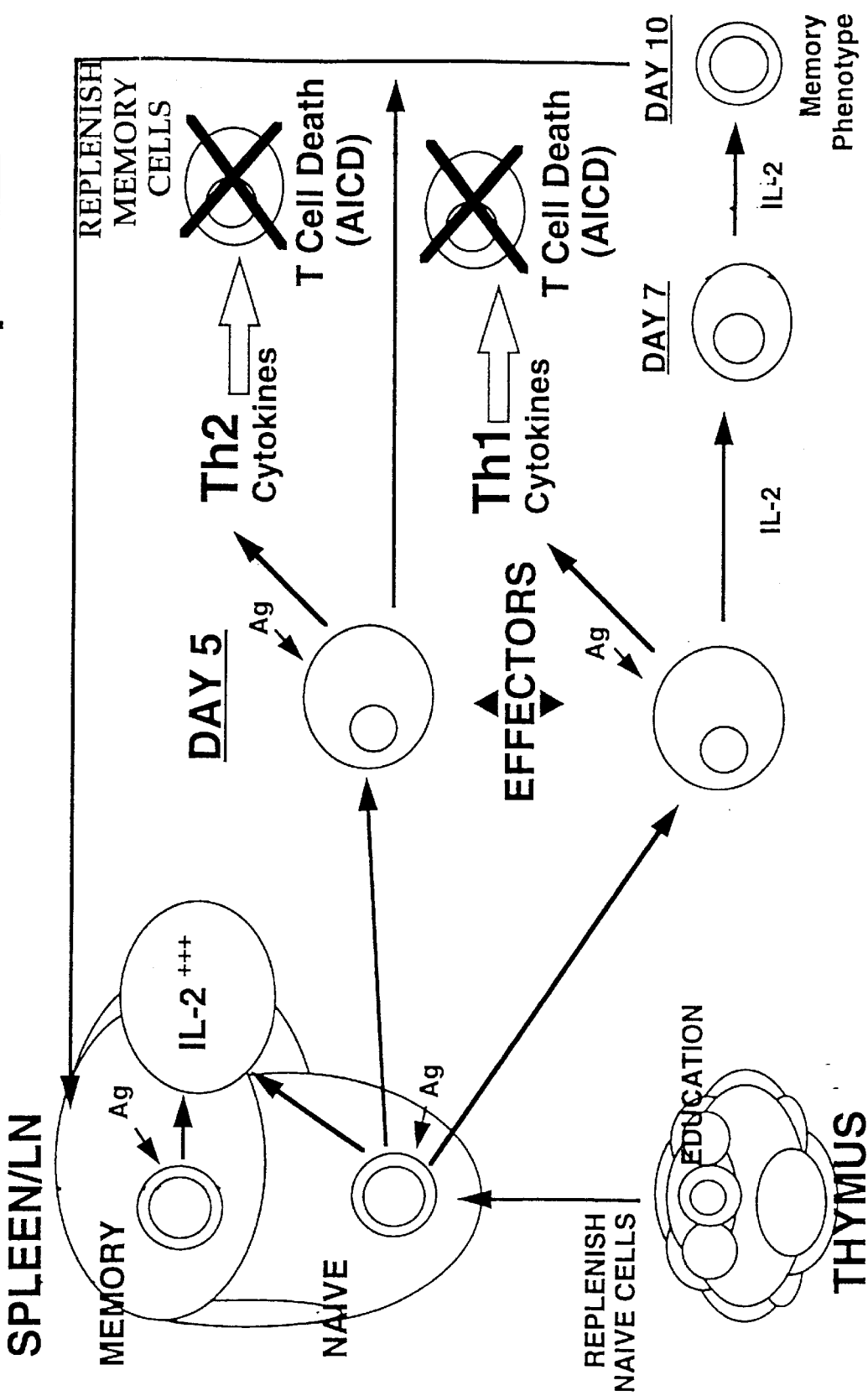
FIG. 1 is a schematic representation of a proposed mechanism of immune system CD4 T-cell activation and response.

To facilitate review and understanding of the invention as described herein, the following definitions of terms are provided:

OX-40 receptor: a protein (also variously termed ACT-4 and ACT35) expressed on the surface of antigen-activated mammalian CD4$^+$ T-cells (Weinberg et al., 1994, 1996; WO 95/12673 (Stanford Univ & Becton Dickinson: W Godfrey et al); Latza et al., 1994). DNA sequences encoding mouse, rat and human OX-40 receptor homologs have been cloned and sequenced (Mallet et al., 1990; Calderhead et al., 1993; Latza et al., 1994; WO 95/12673 (supra)).

OX-40 ligand: a protein (also variously termed gp34 and ACT-4-L) expressed on the surface of certain mammalian cells (such as antigen presenting cells ("APCs")) which specifically interacts with the OX-40 receptor (the protein as such but not its function was described in Miura et al., 1991; WO 95/21915 (Stanford Univ: Godfrey et al) identified the human protein and its function, using the designation ACT-4-L; and U.S. Pat. No. 5,457,035 (Immunex: PR Baum et al.) described a murine protein of corresponding function). Genes encoding the OX-40 ligands from mouse and human have been cloned and sequenced (U.S. Pat. No. 5,457,035 (supra); Miura et al., 1991; Godfrey et al., 1994). The OX-40 ligand includes intracellular, transmembrane and extracellular domains; a functionally active soluble form of OX-40 ligand ("soluble OX-40 ligand") may be produced by deleting the intracellular and transmembrane domains as described in U.S. Pat. No. 5,457,035 and WO 95/21915. A functionally active form of OX-40 ligand is a form that retains the capacity to bind specifically to the OX-40 receptor; methods of determining the ability of an OX-40 ligand molecule or derivative to bind specifically to the OX-40 receptor are discussed below. Methods of making and using the OX-40 ligand and its derivatives are described in WO 95/21915 (supra), which also describes proteins comprising the soluble form of OX-40 ligand linked to other peptides, such as human lg Fc regions, that can be produced to facilitate purification of OX-40 ligand from cultured cells, or to enhance the stability of the molecule after in vivo administration to a mammal (see also U.S. Pat. No. 5,457,035).

As used herein, the term "OX-40L" includes the entire OX-40 ligand, soluble OX-40 ligand, and fusion proteins comprising a functionally active portion of OX-40 ligand covalently linked to a second protein domain. Also included within the definition of OX-40L are OX-40 ligand variants which vary in amino acid sequence from naturally occurring OX-40 ligand molecules but which retain the ability to specifically bind to the OX-40 receptor. Such variants are described in U.S. Pat. No. 5,457,035 and WO 95/21915 (supra).

OX-40 receptor binding agent: an agent which binds substantially only to an OX-40 antigen present on the surface of antigen activated mammalian T-cells, such as activated CD4$^+$ T-cells. As used herein, the term "OX-40 receptor binding agent" includes anti-OX-40 antibodies and OX-40L.

The term "anti-OX-40 antibodies" encompasses monoclonal and polyclonal antibodies which are specific for OX-40, i.e., which bind substantially only to OX-40 when assessed using the methods described below, as well as immunologically effective portions ("fragments") thereof. Preferably, the anti-OX-40 antibodies used in the present invention are monoclonal antibodies (or immunologically effective portions thereof) and preferably humanized monoclonal antibodies (or immunologically effective portions thereof). Immunologically effective portions of monoclonal antibodies include Fab, Fab', F(ab')$_2$, Fabc and Fv portions (for a review, see Better and Horowitz, 1989). In the present invention, immunologically effective portions of monoclonal antibodies are preferably portions including a heavy chain domain. Humanized forms of anti-OX-40 monoclonal antibodies and immunologically effective portions of anti-OX-40 antibodies are described in WO 95/12673 and WO195/21915 (supra), along with methods which may be employed to produce such antibodies. Anti-OX-40 antibodies may also be produced using standard procedures described in a number of texts, including "Antibodies, A Laboratory Manual" by Harlow and Lane, Cold Spring Harbor Laboratory (1988).

Methods of making humanized monoclonal antibodies are well known, and include for example those described in U.S. Pat. No. 5,585,089 (Protein Design: C L Queen et al.; "Humanized Immunoglobulins"), U.S. Pat. No. 5,565,332 ("Production of Chimeric Antibodies-A Combinatorial Approach"), U.S. Pat. No. 5,225,539 (Med Res Council: G P Winter; "Recombinant Altered Antibodies And Methods Of Making Altered Antibodies"), U.S. Pat. No. 5,693,761-762 (Protein Design: C L Queen et al.; "Polynucleotides Encoding Improved Humanized Immunoglobulins", and "Humanized Immunoglobulins"), and U.S. Pat. No. 5,530,101 (Protein Design: C L Queen et al.; "Humanized Immunoglobulins"), and references cited therein.

Similarly, methods of making and using immunologically effective portions of monoclonal antibodies, also referred to as antibody fragments, are well known and include for example those described in Better and Horowitz (1989) ("Expression of Engineered Antibodies and Antibody Fragments in Microorganisms"); Better et al. (1990) ("Production and Scale-Up of Chimeric Fab Fragments from Bacteria"); Glockshuber et al. (1990) ("A Comparison of Stategies to Stabilize Immunoglobulin $F_v$ Fragments"); and U.S. Pat. No. 5,648,237 (Genentech: P J Carter; "Expression of Functional Antibody Fragments"), U.S. Pat. No. 4,946,778 (Genex: R C Ladner et al; "Single Polypeptide Chain Binding Molecules"), and U.S. Pat. No. 5,455,030 (Enzon: R C Ladner et al; "Immunotherapy Using Single Chain Polypeptide Binding Molecules"), and references cited therein.

Various formulations of OX-40L may be used as OX-40 receptor binding agents in the present invention, including the entire OX-40L molecule, soluble OX-40L, and fusion proteins in which, for example, the extracellular domain of OX-40L is covalently linked to a second protein domain. The second protein domain may serve a number of functions, including enhancing the activity of OX-40L, facilitating purification, or increasing the stability of the protein in the body. In such fusion proteins, OX-40L, preferably as an extracellular domain or other active fragment thereof or the mutein of such a domain or fragment, is fused with a suitably chosen protein such as a blood protein or fragment thereof corresponding to suitably chosen blood proteins of the subject to be treated. The specific example described below involves a fusion between OX-40L extracellular domain and a polypeptide representing a constant domain of human IgG, particularly the CH2 and CH3 domains of IgG. Preferably such fusions will include a hinge amino acid sequence region corresponding to a hinge region of the IgG in which preferably any cysteine residues have been mutated to non-sulfur amino acid residues, such as alanine or glycine. It is preferred to have the N-terminal of the OX-40L partial sequence follow on in the fusion protein from the C-terminal of the IgG partial sequence, optionally with a spacer sequence intervening. But the opposite arrangement can also be useful and is also encompassed within the scope of the invention. An alternative example of a fusion partner involves use of domains 3 and 4 of the CD4 sequence in place of the CH2 and CH3 regions of IgG. Such fusion proteins can be made in any suitable heterologous expression system, and, where appropriate, the DNA encoding the fusion protein can also encode a known secretory signal sequence suitable for the host cell system employed so that the DNA is translated into a protein that at first includes the secretory signal and the cleavage sequence but is then transported out of the cell without such ancillary sequences.

An example of a recombinant form of OX-40L is OX-40L:HuFcIgG in which the extracellular domain of OX-40L is fused to the heavy chain of human IgG. The production of such fusion proteins is described in U.S. Pat. No. 5,457,035. By way of example, the OX-40L: HuFcIgG fusion used in the experiments described below was produced as follows. The fusion protein OX40L:huFcIgG was expressed in the well-known CHO cell expression system, using G418 selection and the known pGEM-T cloning vector system. A leader sequence comprising a secretory signal appropriate to the CHO cell expression system was constructed using synthetic oligonucleotides, and annealed and ligated to form an approximately 90 bp fragment. Following assembly, the DNA was excised from an agarose gel and amplified in a PCR reaction using specific primers to generate HindIII and XhoI sites at the termini. The leader was then cloned into the pGEM-T cloning vector to form a product vector comprising the leader sequence. The leader sequence further included bases to encode 7 amino acid resides derived from the antibody heavy chain sequence to provide a site for cleavage of the signal peptide. A subsequence from a human IgG1 gene (cDNA) comprising hinge, CH2 and CH3 domains was PCR-cloned with the introduction of XhoI and PstI sites at the 5' and 3' ends respectively, to allow ligation to the leader and human OX40L sequences. Following cloning into pGEM-T, a XhoI-PstI fragment was isolated, and ligated into the vector comprising the leader sequence as mentioned above (after that vector had been digested with XhoI and PstI), to form a further result vector comprising leader sequence and hinge-CH2-CH3 regions. The extracellular domain of the human OX40L gene was PCR cloned with the introduction of PstI and HindIII sites at the 5' and 3' ends respectively, and ligated into the cloning vector pGEM-T. Clones of the correct orientation were selected, so that digestion with PstI alone led to the release of a gene fragment containing OX40L and polylinker sequence at the 3' terminus. This fragment was then ligated into the PstI site of the previous result vector, thereby forming a vector encoding the wanted leader-IgG-OX40L fusion construct. The gene construct was then isolated as a HindIII fragment and transferred to an expression vector containing a hCMV promoter to drive expression, and a neoR selectable marker. Clones were screened for inserts in the correct orientation, and then grown up for transfection. This construct was used to transfect CHO cells, and positive CHO clones were selected using G418; fusion protein secretion was detected by incubation of supernatants with OX40-transfected Sp2/0 myeloma cells and detection of binding by flow cytometric analysis. High level secreting cells were bulked up and fusion protein form the supernatant purified on a protein G-Sepharose column. Eluted material was run on a SDS-PAGE (12%) gel and the gel stained with Coomassie blue to confirm purity. For human OX-40 sequence ('ACT-4-h-1'), refer to WO 95/12673, and for human OX-40L sequence ('ACT-4-h-1-L'), refer to WO 95/21915 and documents referred to therein. Other peptides which may usefully be fused to the OX-40 receptor binding agent include soluble MHC class II molecules, other co-stimulatory molecules such as B7.1 and B7.2, and T-cell emhancing cytokines such as IL-2.

The determination that a particular agent binds substantially only to the OX-40 receptor may readily be made by using or adapting routine procedures. One suitable in vitro assay makes use of the Western blotting procedure (described in many standard texts, including "Antibodies, A Laboratory Manual" by Harlow and Lane). To determine that a given OX-40 receptor binding agent, such as a selected fragment of the soluble OX-40L, binds substantially only to the human OX-40 protein, total cellular protein is extracted from human cells that do not express the OX-40 antigen, such as a non-lymphocyte cell (e.g., a COS cell or a CHO cell) transformed with a nucleic acid molecule encoding OX-40. As a negative control, total cellular protein is also extracted from corresponding non-transformed cells. These protein preparations are then electrophoresed on a non-denaturing polyacrylamide gel. Thereafter, the proteins are transferred to a membrane (for example, nitrocellulose) by Western blotting, and the agent to be tested is incubated with the membrane. After washing the membrane to remove non-specifically bound agent, the presence of bound agent is detected by the use of an antibody raised against the test agent conjugated to a detection agent, such as the enzyme alkaline phosphatase; application of the substrate 5-bromo-4-chloro-3-indolyl phosphate/nitro blue tetrazolium results in the production of a dense blue compound by immunolocalized alkaline phosphatase. Agents which bind substantially only to human OX-40 will, by this technique, be shown to bind to the human OX-40 band (which will be localized at a given position on the gel determined by its molecular weight) in the extract from OX-40 transformed cells, whereas little or no binding will be observed in the extract from non-transformed cells. Non-specific binding of the agent to other proteins may occur and may be detectable as a weak signal on the Western blots. The non-specific nature of this binding will be recognized by one skilled in the art by the weak signal obtained on the Western blot relative to the strong primary signal arising from the specific agent/human OX-40 protein binding. Ideally, an OX-40 receptor binding agent would not bind to the proteins extracted from the non-transformed cells.

In addition to binding assays using extracted proteins, putative OX-40 receptor binding agents may be tested to confirm their ability to bind substantially only OX-40 receptor in vivo by conjugating the agent to a fluorescent tag (such as FITC) and analyzing its binding to antigen activated CD4$^+$ T-cell and non-activated T-cell populations by Fluorescence Activated Cell Sorting (FACS). An agent which binds substantially only the OX-40 receptor will stain only activated CD4$^+$ T-cells.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid or protein) has been substantially separated or purified away from other biological components in the cell of the organism in which the component naturally occurs, i.e., other chromosomal and extrachromosomal DNA and RNA, and proteins. Nucleic acids and proteins which have been "isolated" thus include nucleic acids and proteins purified by standard purification methods. The term also embraces nucleic acids and proteins prepared by recombinant expression in a host cell as well as chemically synthesized nucleic acids.

Purified: The term purified does not require absolute purity; rather, it is intended as a relative term. Thus, for example, a purified OX-40 ligand preparation is one in which the OX-40 ligand is more pure than the ligand in its natural environment within a cell. Preferably, a preparation of an OX-40 ligand is purified such that the OX-40 ligand protein represents at least 50% of the total protein content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Mammal: This term includes both human and non-human mammals. Similarly, the term "patient" includes both human and veterinary subjects.

2. Compositions and Methods of Enhancing Antigen Specific Immune Response In Animals The enhancement of an antigen-specific immune response in a mammal by engaging the OX-40 receptor on CD4 T-cells during or after antigen activation can be accomplished using a wide variety of methods. The method of choice will primarily depend upon the type of antigen against which it is desired to enhance the immune response, and various methods available are discussed below. Whatever method is selected, the purified OX-40 receptor binding agent should be administered to the animal such that it is presented to T-cells of the animal during or shortly after priming of the T-cells by the antigen. Since the activation of T-cells generally takes place within about 3–7 days after an antigen is presented to the immune system, it is generally preferable to administer the OX-40 receptor binding agent to the animal by the selected method within about 7 days after the immune system of the animal is exposed to the antigen. Where the OX-40 receptor binding agent is administered simultaneously with the antigen, it may be advantageous to administer a form of the agent which has enhanced stability (i.e., increased half-life) in the body so that the agent will remain in the circulatory system for a sufficient period of time to engage with OX-40 receptor during or after antigen priming. Forms of OX-40 receptor binding agent having such enhanced stability include fusion proteins comprising the soluble OX-40 ligand fused to, for example, the constant region of human IgG. To determine the half-life of any selected OX-40 receptor binding agent, standard methods may be used. For example, after administration of the agent by intravenous injection, a small blood sample is removed from the animal, with subsequent samples being taken every 6–24 hours over the period of about 10 days. Thereafter, the concentration of the agent present in each sample is determined (e.g., using standard immunological quantification methods, such as those discussed in Harlow & Lane, 1988, e.g., ELISA). The half-life of the agent is defined as that time point at which the concentration of the agent falls to 50% of that in the first sample measurement.

In some situations, for example where the antigen is presented to the immune system over an extended duration (for example, in cancer patients), the OX-40 receptor binding agent may be administered more than 7 days after the immune system is exposed to the antigen. For example, following surgical removal of a primary tumor from a patient, an OX-40 receptor binding agent may be administered to enhance the immune response to tumor antigens present on metastases, thereby promoting the clearance of such metastases from the body. In such a situation, administration of the OX-40 receptor binding agent will usually occur more than 7 days after the immune system of the patient was first exposed to the tumor antigens, but will nevertheless be present when the antigens are being presented to T-cells.

While the molecule which engages the OX-40 receptor will typically be a protein, such as an anti-OX-40 antibody or an OX-40 ligand, the preparation administered to the mammal may take a number of forms, including a preparation of a purified OX-40 receptor binding agent, a nucleic acid molecule which encodes the OX-40 receptor binding agent, a cell or a virus which expresses the OX-40 receptor binding agent, or a preparation derived from such a cell or virus.

In its simplest form, the preparation administered to the mammal is an OX-40 receptor binding agent, administered in conventional dosage form, and preferably combined with a pharmaceutical excipient, carrier or diluent. Suitable pharmaceutical carriers may be solids or liquids, and may include buffers, anti-oxidants such as ascorbic acid, other polypeptides or proteins such as serum albumin, carbohydrates, chelating agents and other stabilizers and excipients. Suitable solid carriers include lactose, magnesium stearate, terra alba, sucrose, talc, stearic acid, gelatin, agar, pectin, acacia and cocoa butter. The amount of a solid carrier will vary widely depending on which carrier is selected, but preferably will be from about 25 mg to about 1 g per dose of active agent. Suitable liquid carriers include neutral buffered saline, optionally with suitable preservatives, stabilizers and excipients. The carrier or diluent may also include time delay material well known to the art such as, for example, glycerol distearate, either alone or with a wax. The foregoing examples of suitable pharmaceutical carriers are only exemplary and one of skill in the art will recognize that a very wide range of such carriers may be employed. Liposome-based delivery systems may also be employed to deliver OX-40 receptor binding agents. Liposome-based systems, which may be employed to provide a measured release of the agent over time into the bloodstream, are well known in the art and are exemplified by the systems described in U.S. Pat. No. 4,356,167 (Sandoz: L A Kelly; "Liposome drug delivery systems"), U.S. No. 5,580,575 (ImaRx: E C Unger et al.; "Therapeutic drug delivery systems"), U.S. Pat. No. 5,595,756 (Inex Pharm and Univ of BC: M B Bally et al.; "Liposomal compositions for enhanced retention of bioactive agents") and U.S. Pat. No. 5,188,837 (Nova Pharm: A J Domb; "Lipospheres for controlled delivery of substances"), and documents cited therein.

The formulation of the OX-40 receptor binding agent with a pharmaceutical carrier can take many physical forms, but is preferably a sterile liquid suspension or solution, suitable for direct injection. Preferably, the patient will be administered the OX-40 receptor binding agent in a formulation as described above (i.e. in combination with a pharmaceutical carrier), wherein the formulation includes a clinically effective amount of the agent.

As used herein, "a clinically effective amount" is an amount that results in a clinically significant effect. This nature of this effect will vary with the clinical context in which the OX-40 receptor binding agent is being used, for example, whether the agent is being administered as a therapeutic (e.g., to treat an infectious disease, or cancer) or as a prophylactic (e.g., as a vaccine). In the therapeutic context, if the OX-40 receptor binding agent is being administered to a cancer patient, it will be appreciated that any improvement in the patient's condition is clinically significant. Hence, in such a situation, "a clinically effective amount" encompasses amounts of the OX-40 receptor binding agent that result in at least partial remission of the cancer as well as amounts which slow or limit the further progression of the cancer. Similarly, in the therapeutic context where the agent is being used to enhance the immune response of a patient to an infectious agent, such as a virus or a bacterium, where the patient is already infected with the agent, a clinically effective amount is an amount that results in a clinically significant effect, meaning an effect which results in some degree of remission of the infection or the clinical symptoms.

In the prophylactic context, such as vaccination, a clinically effective amount of an OX-40 receptor binding agent is an amount sufficient to provide an enhancement of the immune response to the target antigen, i.e., to produce an immune response greater than would be presented absent administration of the OX-40 receptor binding agent. Quantification of the immune response arising from a vaccination may be achieved in any standard way, e.g., measurement of serum antibody titer for level and/or duration against any convenient test antigen, and/or lymphoproliferation in response to test antigen in vitro.

It will be appreciated that a clinically effective dose of an OX-40 receptor binding agent will vary depending upon the actual OX-40 receptor binding agent being used (e.g., whether it is a soluble OX-40 ligand or an anti-OX-40 antibody fragment), the clinical context (e.g., whether the agent is being used therapeutically or prophylactically), the characteristics of the patient (age, weight, other medications being taken, etc.) and, in the therapeutic context, the severity of the condition. Thus, the assessment of a clinically effective dosage will ultimately be decided by a physician, veterinarian, or other health care worker familiar with the patient. Typically, administering OX-40 receptor binding agent to a mammal according to the methods of the present invention will involve administration of from about 10 ng to 1 g of OX-40 receptor binding agent per dose, with single dose units of from about 10 $\mu$g to 100 mg being commonly used, and specific dosages of up to 1 mg or 10 mg also being within the commonly used range.

For therapeutic applications, the OX-40 receptor binding agent may be administered to a patient through a number of routes, including intravenously or, where the patient has a tumor, directly into the tumor site. The agent may be the sole active ingredient in the composition, or it may be combined with other agents having a beneficial effect, such as an interferon or other immune-stimulatory molecules.

In the prophylactic (vaccine) context, the OX-40 receptor binding agent may be administered to an animal in combination with a conventional vaccine preparation, such as a vaccine preparation comprising bacterial or viral antigens. The OX-40 receptor binding agent may be combined with the conventional vaccine, or may be administered as a separate preparation along with the conventional vaccine. As noted above, the selection of an appropriate OX-40 receptor binding agent will be made to ensure that the agent remains in the circulatory system long enough to engage OX-40 receptors on T-cells during antigen priming (i.e., about 3–7 days after administration of the antigen). Preferably, where the OX-40 receptor binding agent is administered separately, it is administered within about a week of the vaccine being administered. Conventional vaccine preparations suitable for use in the present invention include those prepared with purified bacterial antigens, heat killed bacteria, subunit vaccines and viral vaccines based on live or attenuated virus.

Where the OX-40 receptor binding agent is administered to the mammal in a single preparation with the vaccine antigens, the preparation may be formulated simply by mixing a clinically effective amount of an OX-40 receptor binding agent to the antigen preparation. Alternatively, the OX-40 receptor binding agent may be produced along with the antigen. For example, where the antigen to be administered as a vaccine is a bacterial antigen or a mixture of bacterial antigens, the bacterium from which the antigen preparation is prepared may be a transgenic bacterium which expresses the OX-40 receptor binding agent. In such a situation, the OX-40 receptor binding agent is directly obtained in combination with the bacterial antigens. Similarly, vaccines comprising tumor antigens and OX-40 receptor binding agent may be prepared from tumor cells which express the OX-40 receptor binding agent. Methods of expressing proteins such as OX-40 ligand in transgenic prokaryotic and eukaryotic cells are well known and are described in standard laboratory texts such as Sambrook et al. (1988).

In other embodiments, the present invention contemplates that the immune response of a mammal to a particular antigen may be enhanced by administering to the mammal a nucleic acid molecule which encodes an OX-40 receptor binding agent. Such a nucleic acid molecule is preferably administered either within a cell, or as part of a viral genome, but may also be administered directly as a "naked" nucleic acid molecule. For example, a nucleic acid molecule encoding an OX-40 receptor binding agent may be introduced into an attenuated bacterium (i.e., a form of the organism which does not cause significant disease when administered to a mammal) in a plasmid vector such that the OX-40 receptor binding agent is expressed on the surface of the bacterium. The bacterium may be administered to the mammal in the same manner as a conventional attenuated bacterium vaccine. Alternatively, the nucleic acid molecule encoding the OX-40 receptor binding agent may be introduced into the genome of a virus that is used as a live attenuated vaccine. Attenuated viruses include those in which an essential gene has been deleted, as described in U.S. Pat. Nos. 5,665,362 and 5,837,261 (Cantab Pharmaceuticals: Inglis et al.). Viruses suitable for this purpose include DNA viruses, such as adeno, herpes, papova, papilloma and parvo viruses, as well as RNA viruses such as poliovirus and influenza virus. Methods of preparing viruses carrying heterologous nucleic acid sequences that may be used as viral vaccines are described in U.S. Pat. Nos. 5,665,362 and 5,837,261 (supra), U.S. Pat. No. 5,338,683 (Health Research: E Paoletti) and U.S. Pat. No. 5,494,807 (E Paoletti).

In another embodiment, a nucleic acid encoding an OX-40 receptor binding agent may be introduced into a tumor cell. In many cancer patients, the tumor cells escape detection by the immune system by mechanisms such as down-regulating MHC and/or co-stimulatory molecule expression. Accordingly, one method of treatment previously proposed has been to remove tumor cells from the patient and introduce into them nucleic acids encoding, for example, MHC class II, the co-stimulatory molecule B7 and the stimulatory/adhesion molecule CD2 (see, for example, European Patent Application publication number EP 0 733 373 and references cited therein). Applying the discovery disclosed herein to those methods, introducing a nucleic acid molecule encoding an OX-40 receptor binding agent into tumor cells is expected to provide considerable benefit.

All types of tumor are potentially amenable to treatment by this approach including, for example, carcinoma of the breast, lung, pancreas, ovary, kidney, colon and bladder, as well as melanomas and sarcomas. Nucleic acid molecules encoding a OX-40 receptor binding agent are incorporated into a vector suitable for expression of the OX-40 receptor binding agent in tumor cells. Suitable vectors include plasmid, cosmid and viral vectors, such as retroviruses, adenoviruses and herpesviruses. Disabled viruses, such as those described in U.S. Pat. Nos. 5,665,362 and 5,837,261 may be employed for this purpose. Because of the high efficiency with which viral vectors infect mammalian cells, viral vectors are expected to offer advantages over other vector types. In addition to a nucleic acid molecule encoding an OX-40 receptor binding agent, other nucleic acid molecules may also be introduced into the vector to further enhance the immunogenic effect. By way of example, such other nucleic acid molecules include nucleic acids encoding MHC class II proteins (including $\alpha$ and $\beta$ subunits), and other co-stimulatory molecules, such as B7.1 and B7.2. If desired, a nucleic acid molecule encoding a selectable marker may also be introduced into the vector, such that those tumor cells successfully transformed with the vector can be readily selected.

The vector is then introduced into the tumor cell by one of a range of techniques, such as electroporation, lipofection, co-cultivation with virus-producing cells, or other standard means. In a preferred embodiment, the tumor cells are cells removed from the patient to be treated, but the tumor cells may alternatively be cells from a tumor cell line, such as the human tumor cell lines available from the American Type Culture Collection (ATCC).

If it is desired to screen the cells to select those into which the vector was introduced, this may be achieved by a number of means, including selecting for expression of the selectable marker if one is used, or screening for expression of the OX-40 receptor binding agent on the surface of the cells. This latter procedure may be conveniently performed using a fluorescence activated cell sorter (FACS).

The tumor cells are subsequently administered to the patient in combination with a suitable carrier such as buffered water, saline, or glycine. In a preferred embodiment, where the tumor cells are cells originally removed from the patient, they are attenuated before being administered to the patient. An attenuated cell is one which is metabolically active but which is no longer able to proliferate. Methods for attenuating tumor cells are well known and include those described in EP 0 10 733 373.

In an alternative embodiment, cell membranes from the tumor cells, which include the OX-40 receptor binding agent may be administered to the patient instead of intact tumor cells. A cell membrane preparation can readily be prepared by disrupting or lysing the cells using standard techniques, such as a French Press, freeze-thawing, or sonication. Following disruption of the cells, a membrane enriched fraction may be obtained by centrifugation.

Nucleic acid molecules encoding an OX-40 receptor binding agent may alternatively be administered directly to the patient in the form of "naked" DNA, such that expression of the OX-40 receptor binding agent occurs in the patient's body. Methods of administering naked DNA to animals in a manner to cause expression of that DNA in the body of the animal are well known and are described, for example, in U.S. Pat. No. 5,620,896 (Univ Massachusetts Med Ctr: J E Herrmann et al.; "DNA vaccines against rotavirus infections"), U.S. Pat. No. 5,643,578 (Univ Massachusetts Med Ctr & St Jude Children's Res Hosp: H L Robinson et al.; "Immunization by inoculation of DNA transcription unit") and U.S. Pat. No. 5,593,972 (Wistar Inst & Univ of PA: D B Weiner et al.; "Genetic immunization"), and references cited therein.

The present invention also encompasses other immunotherapy methods for treating conditions such as cancer, including adoptive immunotherapy. As is known in the art, adoptive immunotherapy involves obtaining lymphoid cells exposed to a particular antigen, culturing those cells ex vivo under conditions whereby the activity of the cells is enhanced, and then administering the cells to an individual. The lymphoid cells are preferably T-cells removed from a cancer patient, for example T-cells from a draining lymph node. The present invention teaches that engaging the OX-40 receptor on these cells with an OX-40 receptor binding agent will stimulate these cells and enhance the number of memory cells produced from these cells. Accordingly, one aspect of the present invention is a form of adoptive immunotherapy in which the incubation of lymphoid cells ex vivo is performed in a medium containing an OX-40 receptor binding agent prior to administration of the cells to a patient. The technical details of methods for obtaining lymphoid cells, ex vivo cultivation of such cells with immune stimulants, and administration to patients are known in the field and are described, for example in U.S. Pat. No. 4,690,915 (US DHHS: S A Rosenberg; "Adoptive immunotherapy as a treatment modality in humans"), U.S. Pat. No. 5,229,115 (Immunex: D A Lynch; "Adoptive immunotherapy with interleukin-7"), U.S. Pat. No. 5,631,006 (Endotronics: G B Melink et al.; "Immunotherapy protocol of culturing leukocytes in the presence of interleukin-2 in a hollow fiber cartridge", and U.S. Pat. No. 4,902,288 (M Ingram; "Implantable immunotherapy system using stimulated cells"), and references cited therein.

3. EXAMPLES

The following examples illustrate methods and materials of use in connection with the present invention, and also indicate efficacy of the present invention.

Example 1

Stimulation of Antigen-Specific T-cell with OX-40 Receptor Binding Agent

To demonstrate that OX-40 receptor binding agents can stimulate antigen-specific T-cells, in vitro T-cell proliferation assays were conducted using myelin basic protein (MBP) specific T-cells and anti-OX-40 mAb as the OX-40 receptor binding agent.

After expansion in RPMI and 10% FCS, MBP-specific T cells were harvested, washed, counted and resuspended in media for use in the T-cell proliferation assay described by Vandenbark et al. (1985). $2 \times 10^5$ T cells were stimulated in 96-well flat bottom plates for 48 hours in stimulation medium, and pulsed for 18 hr with 1 $\mu$Ci[$^3$H]-TdR. The cells were harvested and mean thymidine incorporation (cpm) was calculated from triplicate wells. Monoclonal antibodies to rat CD3, OX-40, and CD28 were commercially obtained from Pharmingen (La Jolla, Calif.).

Figure 2:
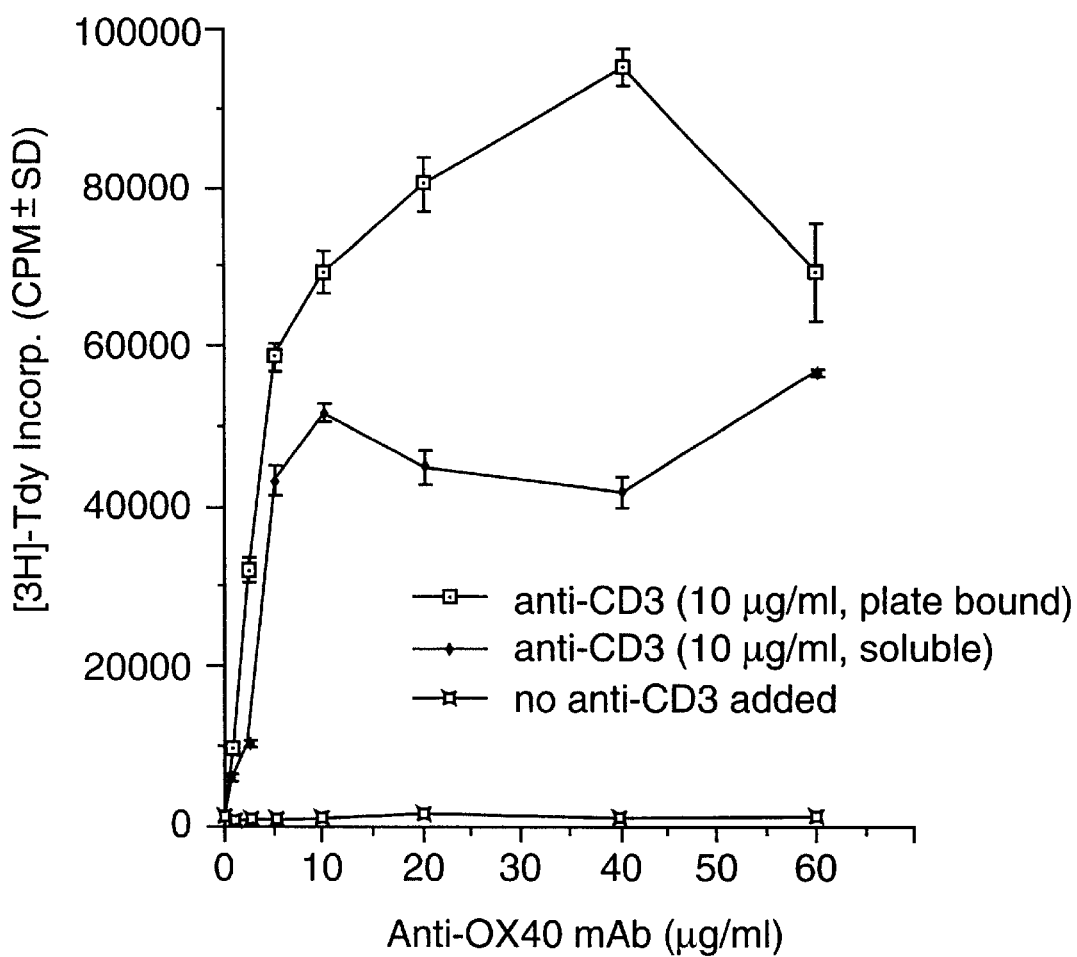
FIG. 2 is a graph showing the effect of engaging the OX-40 receptor on T-cell proliferation in vitro.

To examine the effect of OX-40L on T-cell proliferation in vitro, T-cells were seeded in a 96-flatwell plate at $2 \times 10^5$/well and stimulated with 10 $\mu$g/ml of either soluble or plate-bound anti-CD3 plus increasing concentrations of anti-OX-40 antibody. The cells were cultured for 48 hr, labeled with $^3$[H]-thymidine for 18 hr, and were then harvested and counted. The results, shown in FIG. 2, are presented as mean CPM with standard deviation calculated from triplicate wells. The results indicate that the OX-40 receptor binding agent (i.e., the anti-OX-40 mAb) produced a dose-dependent costimulation/stimulation (mitogenesis) of the MBP specific CD4$^+$ T-cells.

Example 2

OX-40 Receptor Engagement is at Effector Stage

To determine the stage of T-cell development (i.e., naive or effector cell) at which OX-40 receptor engagement is effective, a fibroblast cell line expressing the murine IE$^k$ MHC class II molecule was utilized (Dubey et al., 1995). This cell line can present antigen (pigeon cytochrome c, (PCC)) to T-cells from the T-cell receptor transgenic mice described by Kaye and Hedrick (1989). Using this cell line, a transgenic fibroblast cell line was produced which expresses OX-40 ligand and can stimulate splenic CD4$^+$ T-cells from the T-cell receptor transgenic mice.

Experiments comparing the effect of stimulating naive T-cells taken directly from the mice with PCC antigen in combination with fibroblasts expressing (1) MHC class II alone, (2) MHC class II and B7.1, (3) MHC class II and OX-40 ligand, or (4) MHC class II, OX-40 ligand and B7.1 showed that the MHC class II/OX-40 ligand/B7.1 combination was the best stimulator of naive T-cells (data not shown).

Figure 3:
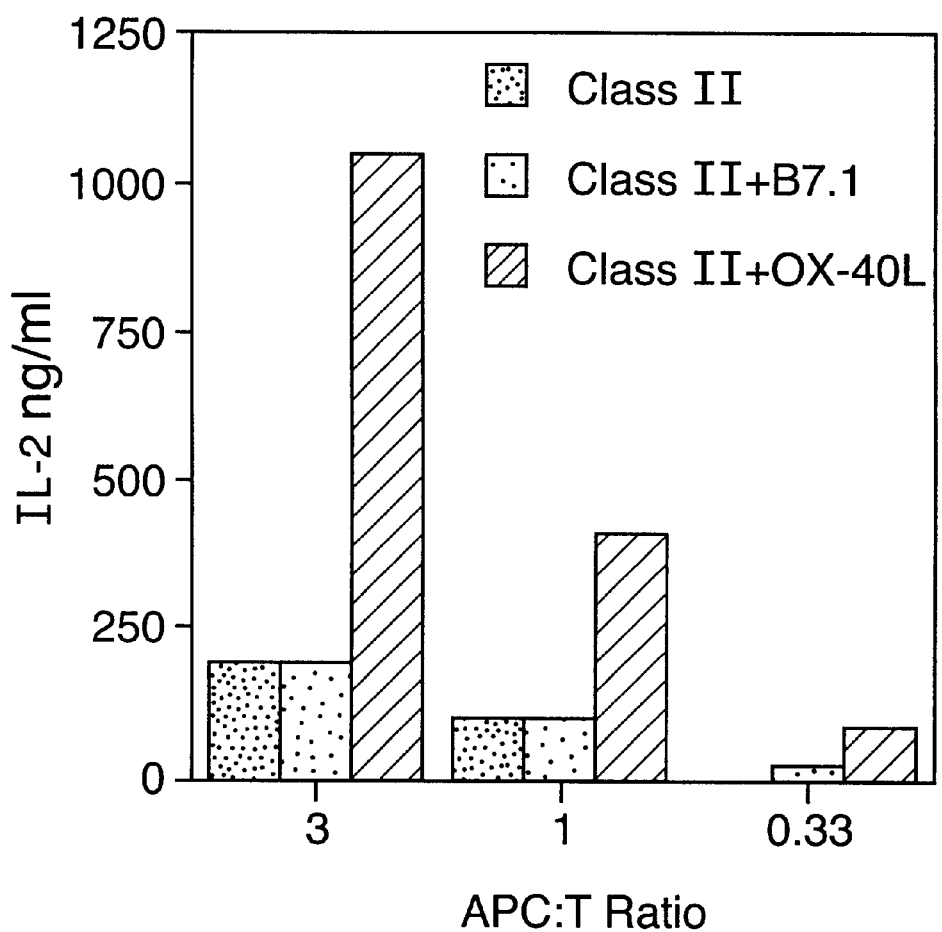
FIG. 3 is a graph showing a comparison of the levels of IL-2 produced by T-cells restimulated with APCs expressing either MHC class II alone, MHC class II plus B7.1 or MHC class II plus OX-40 ligand.

Thereafter, naive T-cells taken directly from the animals were stimulated with PCC antigen and fibroblasts expressing MHC class II and B7.1, to produce effector cells. These effector cells were then expanded in IL-2 for 5 days, washed and restimulated with PCC antigen and in combination with fibroblasts expressing (1) MHC class II alone, (2) MHC class II and B7.1 or (3) MHC class II and OX-40 ligand. The experiment was performed using three different ratios of APC:T-cells, and the effect of this second stimulatory event was measured by quantifying IL-2 production. The results, depicted in FIG. 3, showed that presentation of the antigen by APCs expressing MHC class II and the OX-40 ligand was the most potent stimulator of the effector stage T-cells. Accordingly, it appears that OX-40 receptor engagement is more important at the effector T-cell stage, suggesting that engagement of the OX-40 receptor plays a role in the development of CD4$^+$ T-cells at the effector stage and may enhance memory cell development. This clearly differentiates the effect of costimulation by OX-40L from co-stimulation by previously described co-stimulatory molecules, which act at the naive cell to effector cell transition.

Example 3

OX-40 Receptor Binding Agent Induces Tumor Resistance

To demonstrate the effect of providing OX-40 receptor binding agent to T-cells during tumor priming in vivo, experiments were performed using soluble OX-40L fused to the Fc portion of human IgG ("OX-40L:HuFcIgG") as the OX-40 receptor binding agent.

The inoculation protocol for this series of experiments was performed by subcutaneously inoculating mice on day 0 with between $1-3 \times 10^5$ MCA 303 sarcoma tumor cells (Huntzicker & Fox, 1995). Three days later the animals were given intraperotineal injections with OX-40L:HuFcIgG, and were given a second dose on day 7 after tumor inoculation (the dose varied depending upon the experiment, see details below). The animals were then monitored for tumor growth for 50 days or greater. Animals were sacrificed when the tumors became 0.3 in² in size.

Figure 4:
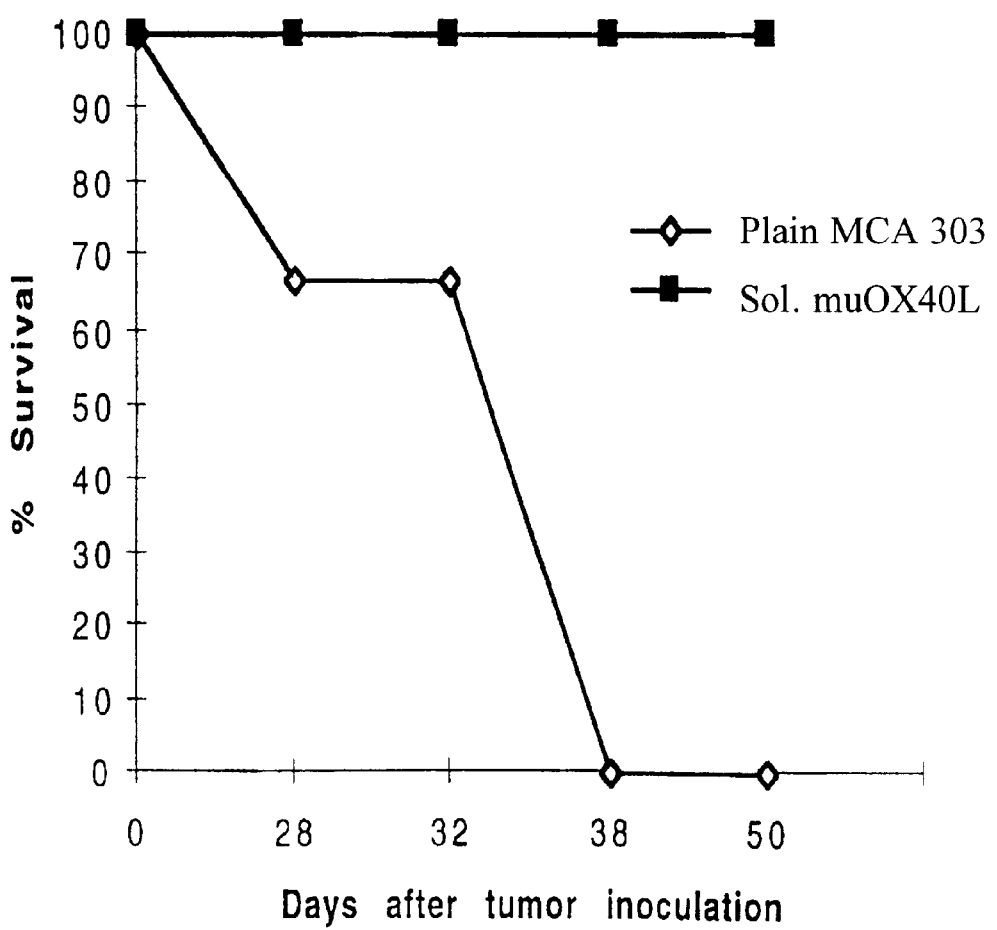
FIG. 4 is a graph illustrating the protective effect of administering OX-40 receptor binding agent to mice inoculated with tumor cells.

FIG. 4 shows the remarkable effect of soluble OX-40 ligand injected i.p. on 3 day established tumor. Six animals were injected with 3×10⁵ MCA 303 tumor cells that were in vitro passaged. Three animals received 100 μg in 500 μl of RPMI of soluble murine OX-40 ligand i.p. and three animals received 500 μl of RPMI alone, three and seven days after tumor inoculation. The animals were monitored for signs of tumor for 50 days post-inoculation. As shown in FIG. 4, while all of the animals that received tumor cells with no OX-40L died within 38 days, the animals that did receive OX-40L remained tumor-free.

Figure 5:
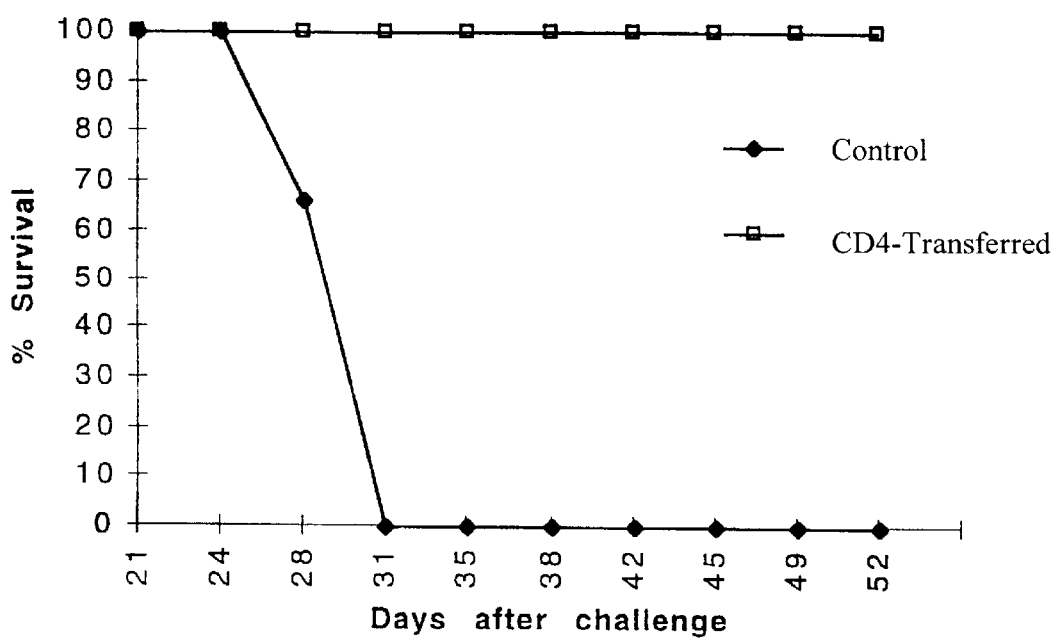
FIG. 5 is a graph showing the protective effect of adoptive transfer of splenocytes from mice inoculated with OX-40 receptor binding agent and tumor cells into naive mice subsequently challenged with tumor cells.

Thereafter, animals that had been treated with soluble OX-40 ligand during tumor priming and had become resistant to tumor challenge were depleted of CD8⁺ T cells by administration of anti-CD8 i.p. These animals were sacrificed and their splenocytes were isolated and phenotyped to show that the CD8⁺ T cells were depleted. The spleen cells were adoptively transferred into naive mice (1 spleen equivalent/mouse), and the recipient mice were challenged with MCA 303 tumor 9 days post-transfer. An equivalent cell number of MCA 303 tumor was inoculated into control naive mice and all animals were monitored for signs of tumor for 50 days post-inoculation. As shown in FIG. 5, while all animals receiving only the tumor cells died within 31 days of administration of the tumor cells, all of the animals receiving the transferred splenocytes from tumor-immune animals remained healthy. This experiment indicates that the effect of administering the OX-40 receptor binding agent to the mice along with the tumor cells produces a sufficient population of tumor antigen specific memory T-cells to confer immunity after adoptive transfer. It is therefore evidence that co-stimulating effector T-cells by engaging the OX-40 receptor is important in the effector/memory cell transition.

Example 4

OX-40 Receptor Binding Agent Confers Resistance to In Vivo Passaged Tumor Cells

Figure 6:
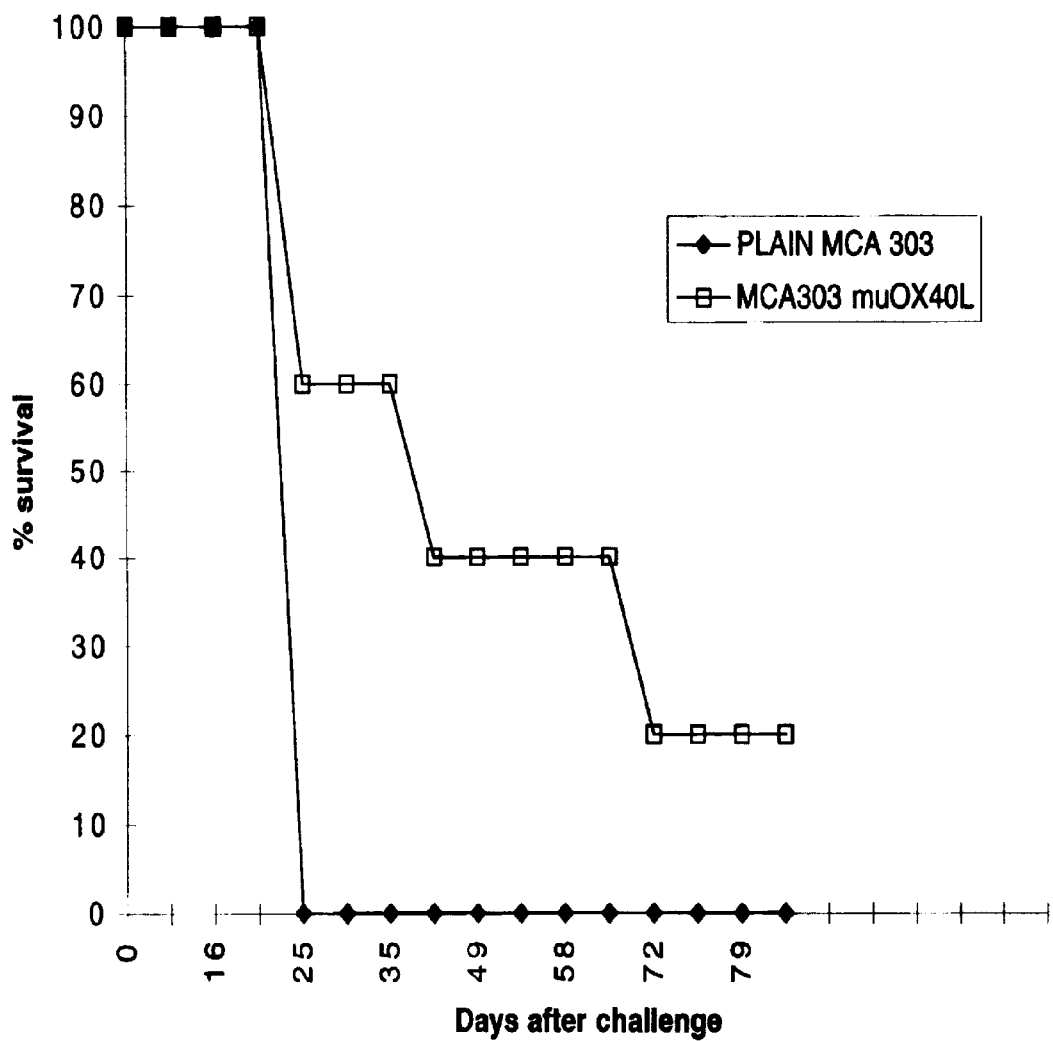
FIG. 6 is a graph showing the protective effect of administering an OX-40 receptor binding agent to mice inoculated with in vivo passaged tumor cells.

The protection conferred by administration of OX-40L described in Example 3 was against in vitro passaged tumor cells. Since in vivo passaged tumor cells are significantly more tumorigenic, the ability of OX-40L to confer protection against in vivo passaged cells was examined. Ten animals were injected subcutaneously with 1×10⁵ MCA 303 cells that were passaged in vivo. Five animals were injected i.p. with 100 μg of soluble OX-40 ligand and five animals were injected with the same volume of RPMI, three and seven days after tumor inoculation. The animals were followed for signs of tumor 80 days post tumor inoculation. The results, shown in FIG. 6 indicate that administration of OX-40L confers enhanced protection even against the highly tumorigenic in vivo passaged tumor cells.

Figure 7:
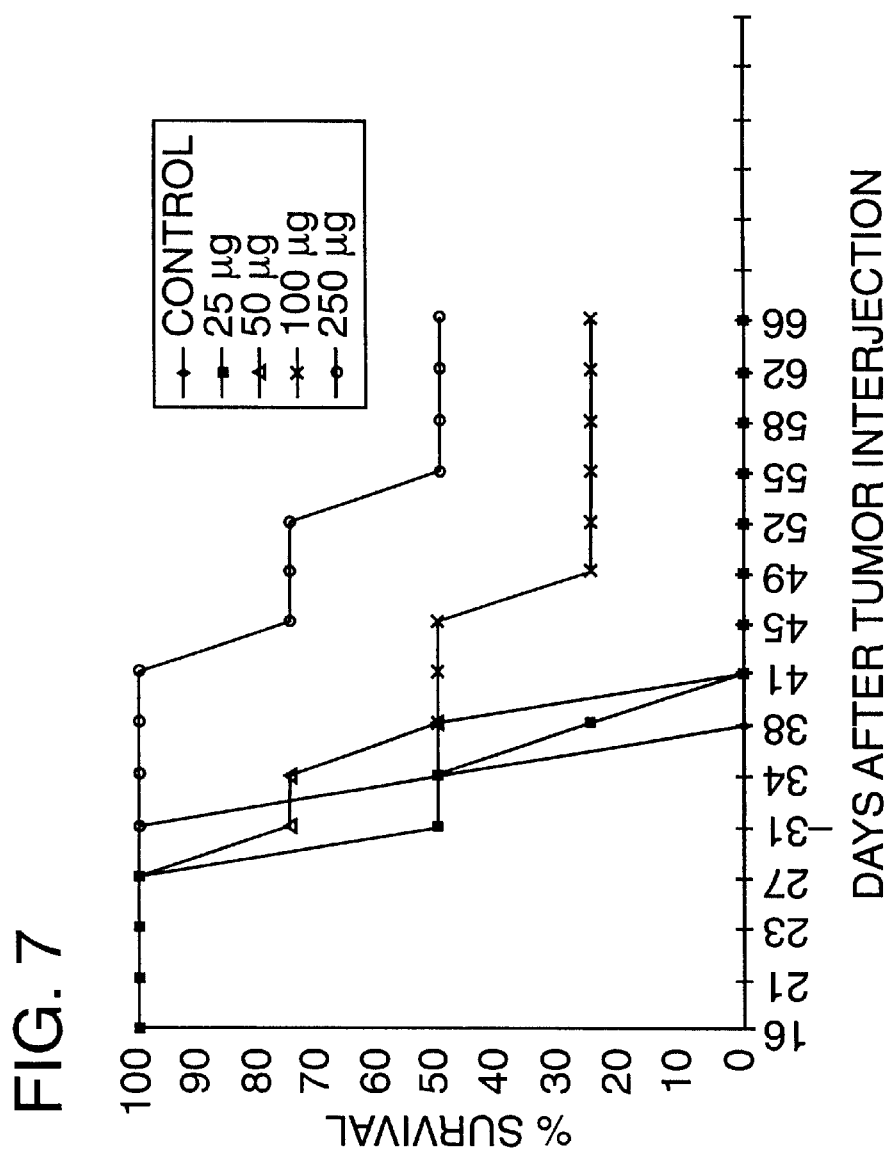
FIG. 7 is a graph showing that the protective effect of the OX-40 receptor binding agent against in vivo passaged tumor cells is dependent on the dose of OX-40 receptor binding agent administered.

The ability of OX-40L to confer protection against in vivo passaged tumor cells was also examined using differing doses of OX-40L. Twenty animals were injected subcutaneously with 1×10⁵ in vivo passaged MCA 303 tumor cells. The animals were separated into 5 groups and were injected with increasing amounts of the soluble OX-40 ligand i.p. on days 3 and 7 after tumor inoculation. The control group received RPMI, while the dose titration was performed with 25, 50, 100, and 250 μg OX-40L per injection. The animals were followed for signs of tumor for 66 days post tumor inoculation. The results, shown in FIG. 7, indicate that the enhanced tumor resistance exhibited by animals receiving OX-40L is dependent on the dose of OX-40L received, and that, even against the virulent in vitro passaged tumor cells, 50% survival is achievable with higher doses of OX-40 receptor binding agent.

Example 5

OX-40 Receptor Binding Agents as Component of Tumor Vaccine

This Example demonstrates the efficacy of OX-40 receptor binding agents in tumor vaccines. A B16-melanoma mouse cell line, F10, which does not express MHC class II or the OX-40 ligand was transfected (with Lipofectin) with the cDNAs for the OX-40 ligand and CIITA. The CIITA cDNA codes for a protein that binds to the MHC class II promoter and potentiates the synthesis and cell surface expression of the endogenous MHC class II genes. These two genes were co-transfected into the parental F10 line and three variants were isolated; 1) MHC class II⁺, 2) OX-40 ligand⁺ and 3) MHC class II⁺ and OX-40 ligand⁺. These transfection variants and the parental line were irradiated with 500 rads and injected subcutaneously into naive animals (2×10⁶ cells/injection) and the vaccination procedure was repeated 14 days later. The immunized animals were challenged with the F10 parental cell line (5×10⁵/animal) injected subcutaneously.

Figure 8:
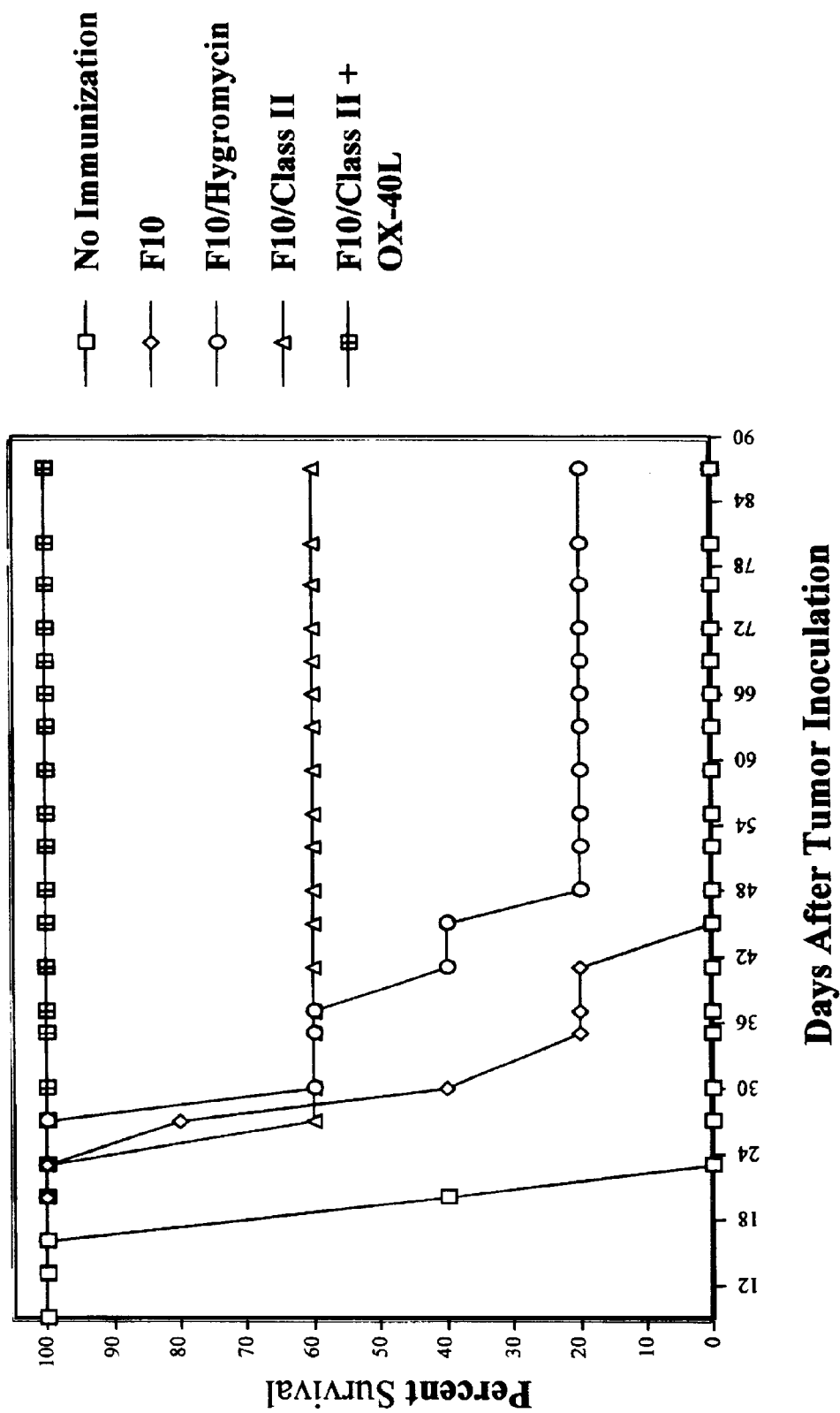
FIG. 8 is a graph showing the protective effective of vaccinating mice with irradiated tumor cells expressing OX-40 receptor binding agent and MHC class II.

FIG. 8 shows the result of an experiment in which naive animals were injected with irradiated parental F10 tumor, F10 tumor that is hygromycin resistant, F10 expressing MHC class II alone, or F10 expressing MHC class II and OX-40 ligand. Two weeks later these animals were challenged with live parental F10 tumor and the animals were followed for signs of tumor for 84 days. As shown in FIG. 8, animals that received no initial immunization succumbed quickly to the F10 tumor cells, whereas initial immunization with the irradiated F10 tumor conferred some degree of protection. Greater protection was seen with animals that were immunized with the irradiated F10 cells expressing MHC class II, and maximal protection was observed when immunization was performed using F10 cells expressing both MHC class II and OX-40L. This result is expected since F10 cells which do not express MHC class II would be greatly impaired in their ability to interact with the T-cell receptor. Many tumor cells down-regulate or completely abolish MHC class II expression. Therefore, in clinical application, it may be advantageous to transform tumor cells removed from a patient with nucleic acid molecules encoding MHC class II and an OX-40 receptor binding agent, before the cells are returned to the patient.

Examples 6–9

In the following further examples, the OX-40 receptor (OX-40R) was engaged with either OX-40 ligand (OX-40L) or an antibody agonist to deliver a costimulatory signal to effector T cells, and this was observed to enhance a tumor-specific T cell response. Injection of OX-40L:Ig or anti-OX-40R in vivo during tumor priming led to a percentage of tumor-free survivors (20–55%) from 4 different tumors derived from 4 separate tissues. The anti-OX40R effect was dose-dependent and accentuated tumor-specific T cell memory. The data of these examples is believed to indicate that engagement of the OX-40R in vivo augments tumor-specific priming by stimulating/expanding the natural repertoire of the host's tumor-specific T cells. The appearance of OX-40⁺ T cells clustered around human tumor cells in vivo also is believed to indicate that this is a practical approach to expand tumor reactive T cells and thereby enhance tumor immunotherapy in patients with cancer.

Example 6

OX-40R Expression In Human Breast Cancer

Figure 9:
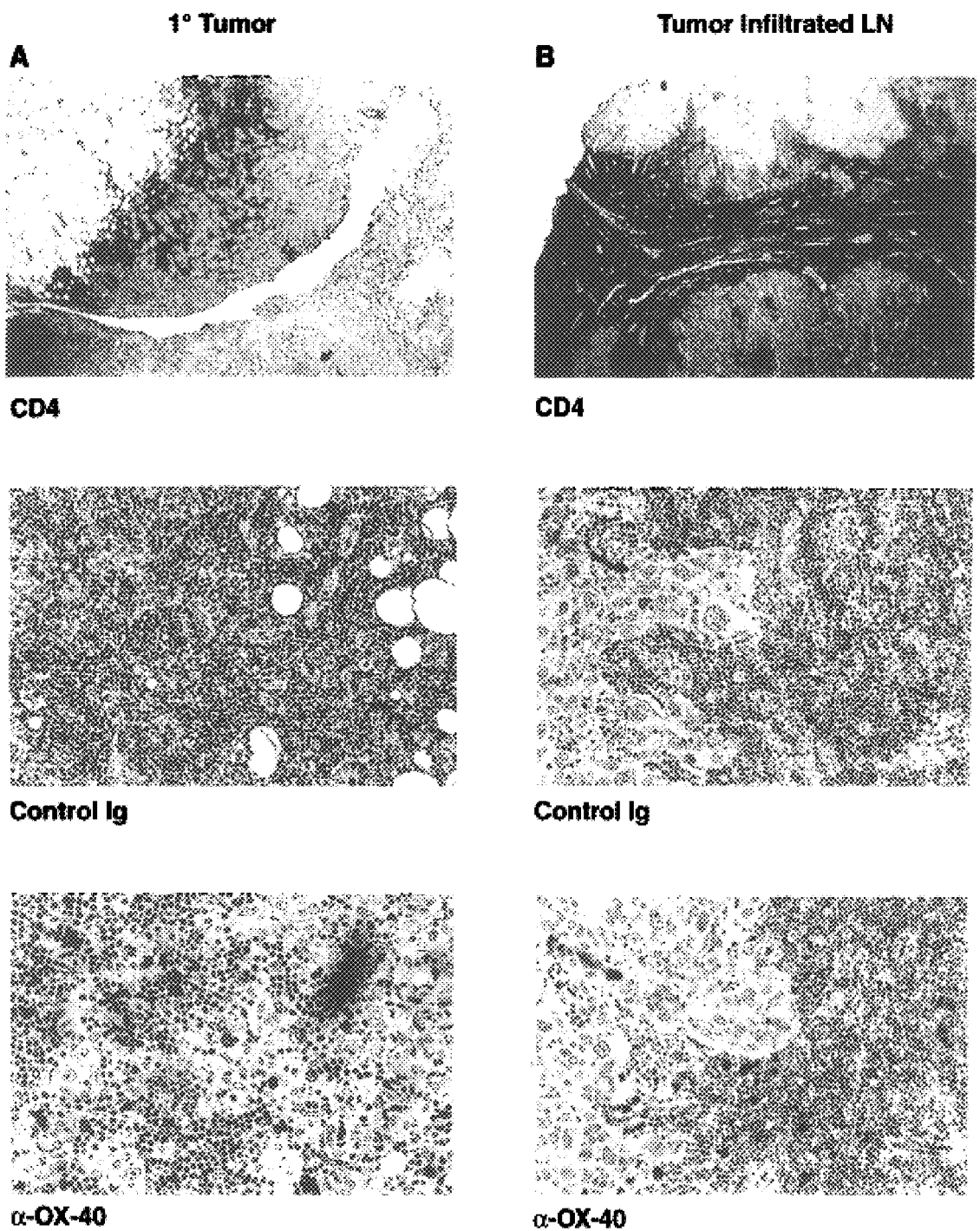
FIG. 9 shows photomicrographs of breast cancer biopsies from two patients with staining to show localisation of lymphocytes and OX40R$^+$ cells, relevant to treatment of such cancers by methods described herein.

In order to determine the spatial relationship between OX-40R$^+$ T cells and tumor cells, several human breast cancer biopsies were examined by immunohistochemistry. Both primary tumors and tumor invaded lymph nodes were analyzed for CD4$^+$ and OX-40R$^+$ cells. FIG. 9 is a representative sample from two separate patients both with infiltrating ductile breast carcinoma. Panel A depicts tumor infiltrating lymphocytes within a 10 tumor, while panel B depicts a tumor infitrated lymph node. Panel A shows that CD4$^+$ cells are infiltrating the tumor around the outer edge of the surgical specimen. The OX-40R$^+$ cells were visualized (at higher magnification) and were a subset of the invading lymphocytes which were in close proximity to the tumor cells. A number of the OX-40R$^+$ cells appear to be larger (blasts) with some exhibiting the appearance of lymphocytes undergoing mitosis. Panel B depicts a lymph node where more than half of the architecture has been invaded by the tumor. There is an abundance of CD4+ cells that surround the invading tumor. The OX-40R$^+$ cells were found concentrated in areas directly adjacent to the invading tumor cells. There were OX-40R$^+$ cells also found in areas that were not invaded by tumor, but the highest percentage were found closest to the site of tumor infiltration. It is believed that OX-40R$^+$ cells within these tissue sections most likely represent tumor-specific T cells.

Example 7

Engaging The OX-40R In Vivo During Tumor Priming (Sarcoma)

Figure 10:
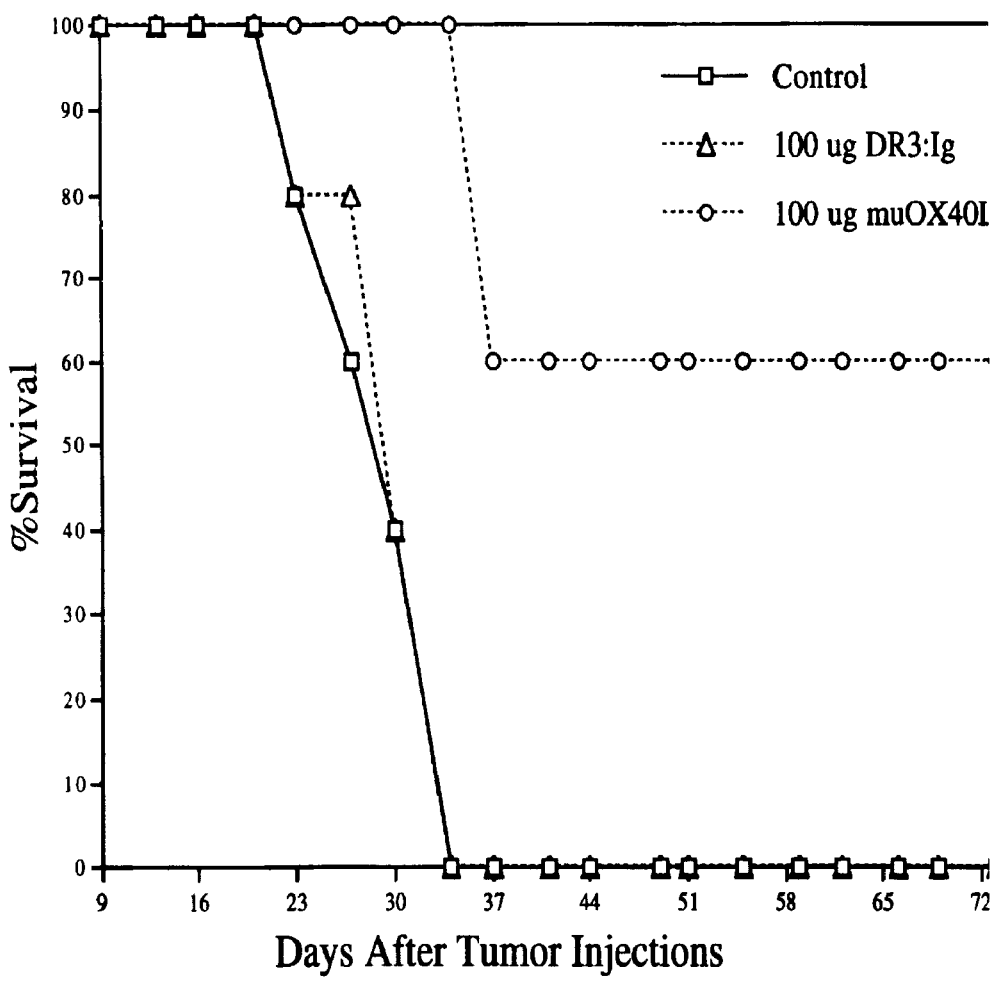
FIGS. 10–14 are graphs showing survival of animals in the experiments of Examples 6–9 below.

Without wishing to be bound by theory, it is believed that OX-40R$^+$ cells at the tumor site or draining lymph nodes are most likely tumor-specific T cells in vivo. Engaging the OX-40R is believed to cause a potent costimulatory response leading to T cell proliferation, increased cytokine production, and enhanced survival of effector T cells. FIG. 10 shows results of tests designed to investigate whether engaging the OX-40R in vivo during tumor priming would lead to an enhanced anti-tumor specific response. FIG. 10 depicts mice that were injected with a lethal inoculum of MCA 303 (methyl-cholanthrene induced sarcoma) subcutaneously (s.c.) and were treated 3 and 7 days later with either mOX-40L:Ig, DR3:Ig, or saline. Mice treated with DR3:Ig had to be sacrificed due to tumor growth with similar kinetics as the mice receiving saline. In contrast, mice that received mOX-40L:Ig were all delayed in tumor growth and 60% remained tumor-free for greater than 70 days. The mOX-40L:Ig protected mice were rechallenged with MCA 303 tumor s.c. and the mice remained tumor-free, believed to indicate that they had developed a tumor-specific memory T cell response.

Figure 11:
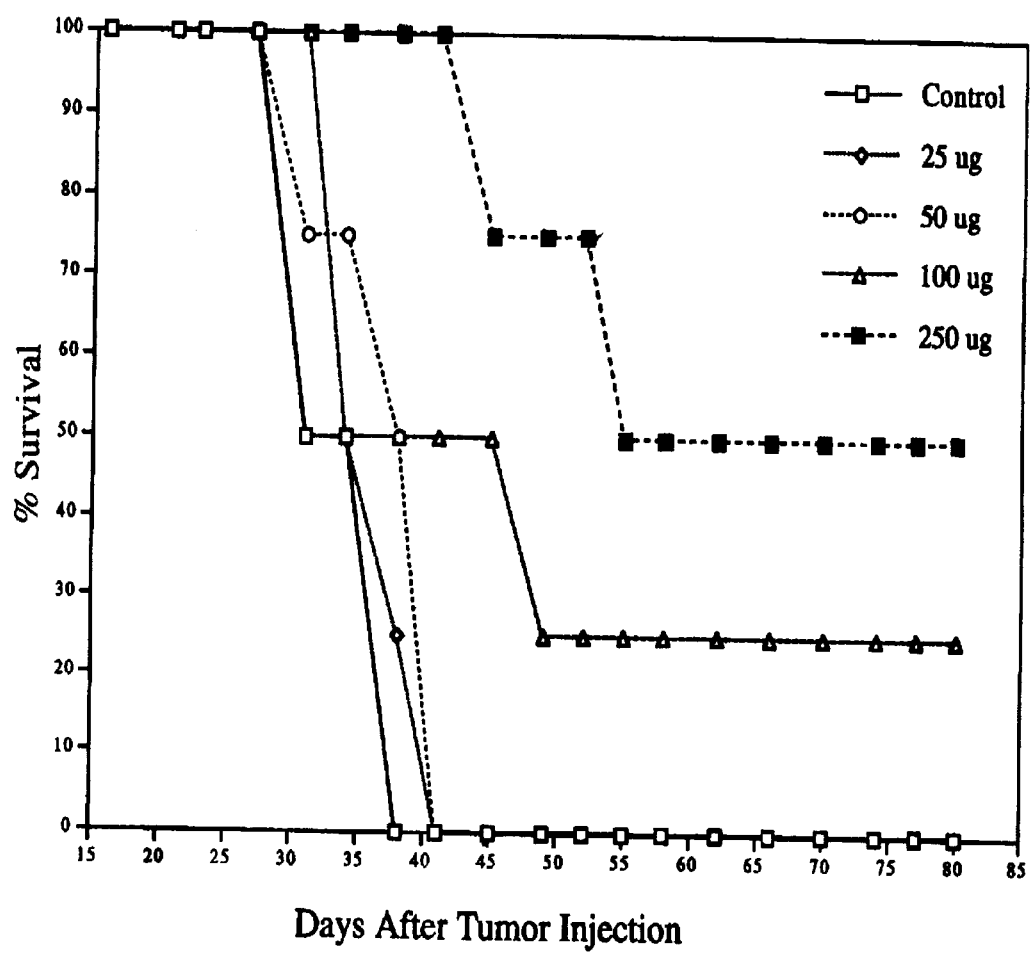

Mice injected with MCA 303 were then subjected to a dose-titration of mOX-40L:Ig on days 3 and 7 post-tumor inoculation. Mice that received 25 or 50 micro-g of mOX-40L:Ig had to be sacrificed due to tumor growth in a similar time frame as the control saline-treated mice. Fifty percent of the mice receiving 100 micro-g of mOX-40L:Ig experienced a delay in tumor growth, while 100% of the mice receiving 250 micro-g were delayed in tumor growth. Ultimately, 25% of the 100 micro-g group and 50% of the 250 micro-g group were tumor-free for more than 70 days post-tumor challenge. It should be noted that the MCA 303 tumor line gets more tumorigenic and less immunogenic the more times that it is passaged in vivo. The MCA 303 tumor line in FIG. 11 had been passaged more times in vivo than FIG. 10, therefore the OX40L:Ig treatment is believed to have given a slightly lesser amount of effect at the 100 micro-g dose.

Figure 12A:
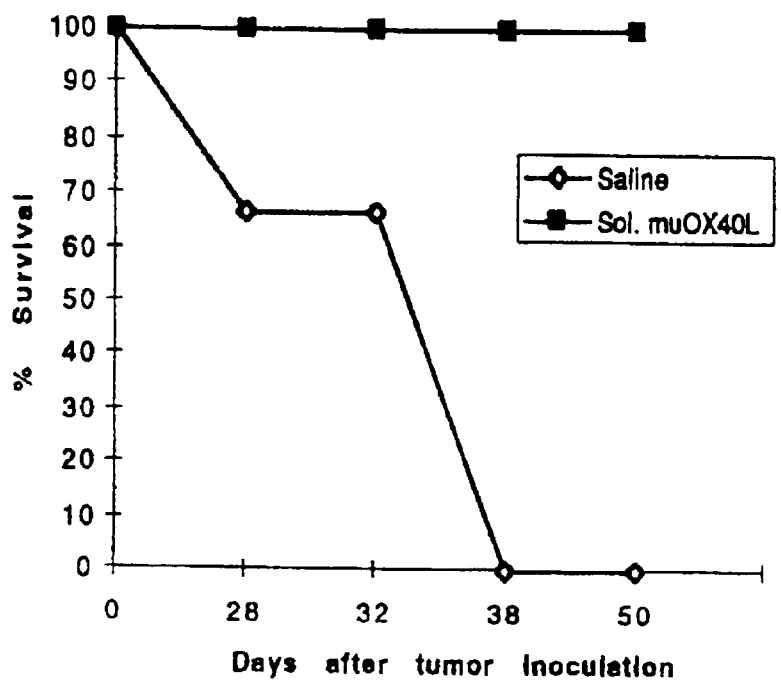
Figure 12B:
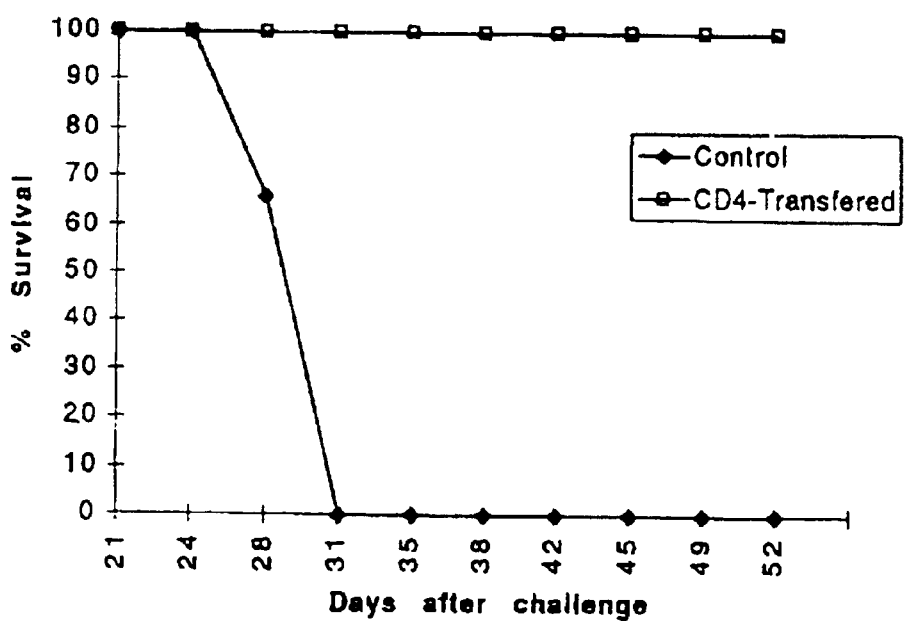

FIG. 12 shows the fate of mice inoculated with in vitro passaged MCA 303 and then treated with mOX-40L:Ig (in vitro passaged MCA 303 was easier to treat). Mice were inoculated with tumor s.c. and injected with mOX-40L:Ig on days 3 and 6 post-tumor inoculation. Panel 4A shows that all the mOX-40L:Ig treated mice survived the initial tumor challenge while all the mice injected with saline had to be sacrificed due to excessive tumor burden. The mOX-40L:Ig treated mice that survived the initial tumor challenge (FIG. 12.A) were then rechallenged with MCA 303 and all the mice were immune to the second challenge for 53 days (data not shown). These same animals were then inoculated with MCA 303 s.c. and 10 days later were depleted of CD8 cells by injecting an anti-Lyt 2 intraperitoneally (i.p.) Three days later these mice were sacrificed and shown to be devoid of CD8 cells (<2%) in the spleen and $1.45 \times 10^{-7}$ of these spleen cells were transferred into naive mice. Fifteen days later the mice were challenged with MCA 303 s.c. and FIG. 12B shows that the mice receiving the CD8 depleted immune cells were resistant to tumor challenge while the control mice had to be sacrificed due to tumor burden.

Example 8

OX-40R Specific Treatment in a Weakly Immunogenic Tumor Model (B16/F10)

Figure 13A:
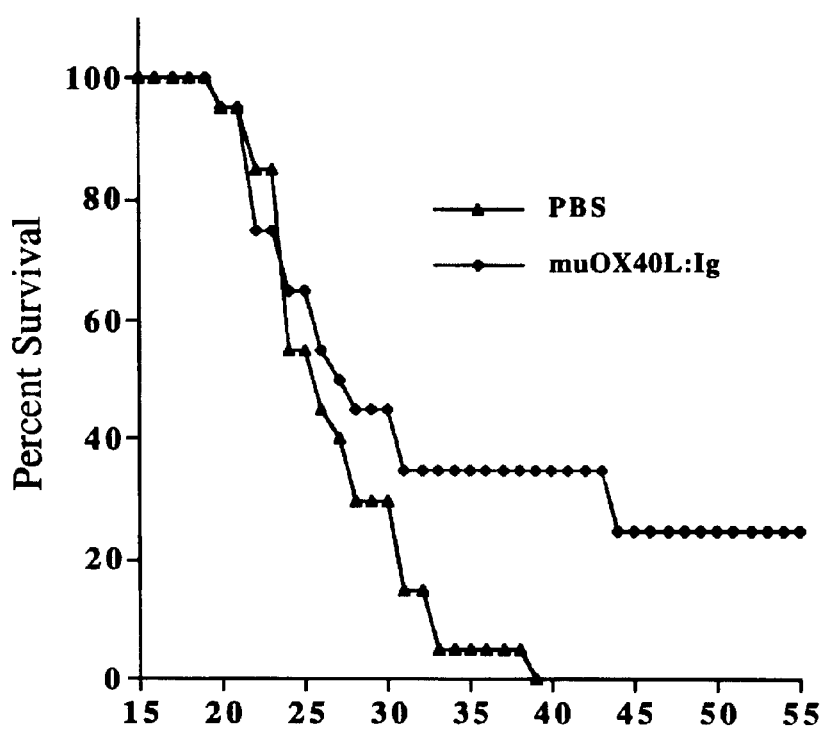
Figure 13B:
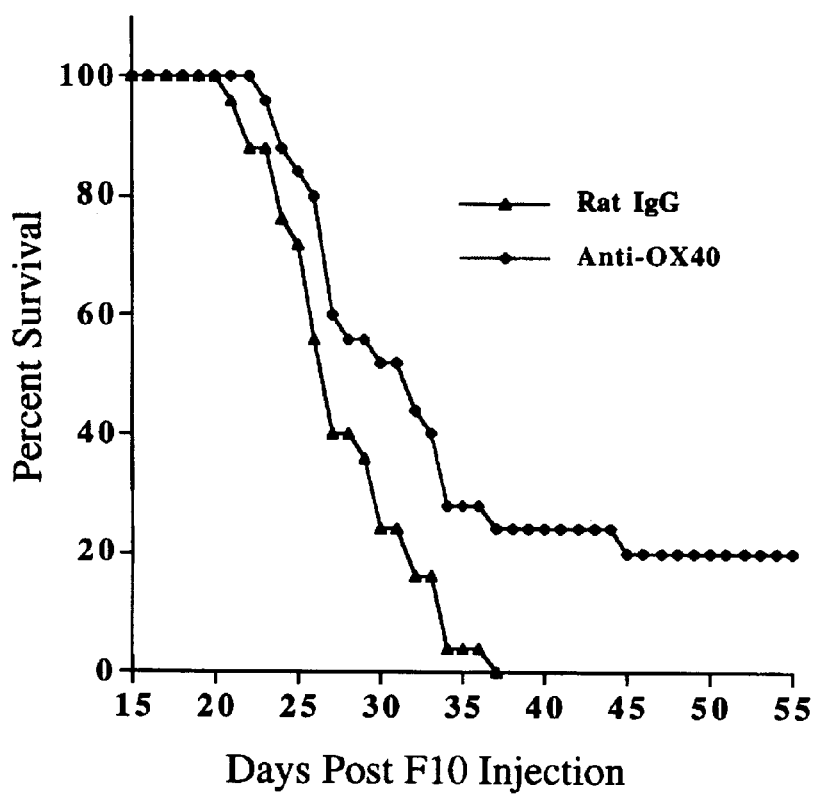

The F10 variant of the B16/B16 melanoma line does not elicit a protective immune response when injected as an irradiated vaccine s.c. (data not shown), and has therefore been characterized as a weakly immunogenic tumor. FIG. 13 shows results of tests designed to determine if engaging the OX-40R during tumor priming would enhance immunity to this aggressive tumor. FIG. 13A shows that treating mice with mOX-40L:Ig on days 3 and 7 post-inoculation with F10 was effective compared to the control mice (approximately 25% survived tumor challenge long-term). FIG. 13B shows that a separate reagent that binds to the OX40R (monoclonal Ab OX-86) delivered at the same dose enhanced tumor-free survival to a similar level as mOX-40L:Ig. The percentage of tumor-free mice for the Ab treatment was very similar to OX-40L:Ig and both reagents were shown to provide statistically relevant tumor protection by log rank ana lysis ($p=0.007$ (Ab) and $0.05$ (mOX-40L:Ig)).

Example 9

Enhancement of Anti-Tumor Immunity in Colorectal Cancer Model (CT26)

A similar protocol was designed to treat mice with CT26 tumor cells injected s.c. as described above (mOX-40L:Ig—two dose regimen). HuOX-40L:Ig was used as a negative control because it does not bind to the murine OX-40R. In an initial experiment the two dose regimen was able to enhance tumor-free survival significantly $p=0.04$ (data not shown). The identical experiment was then performed as above except with multiple injections after tumor inoculation (injections given on days 2, 7, 14, 21, 27, and 40). FIG.

Figure 14A:
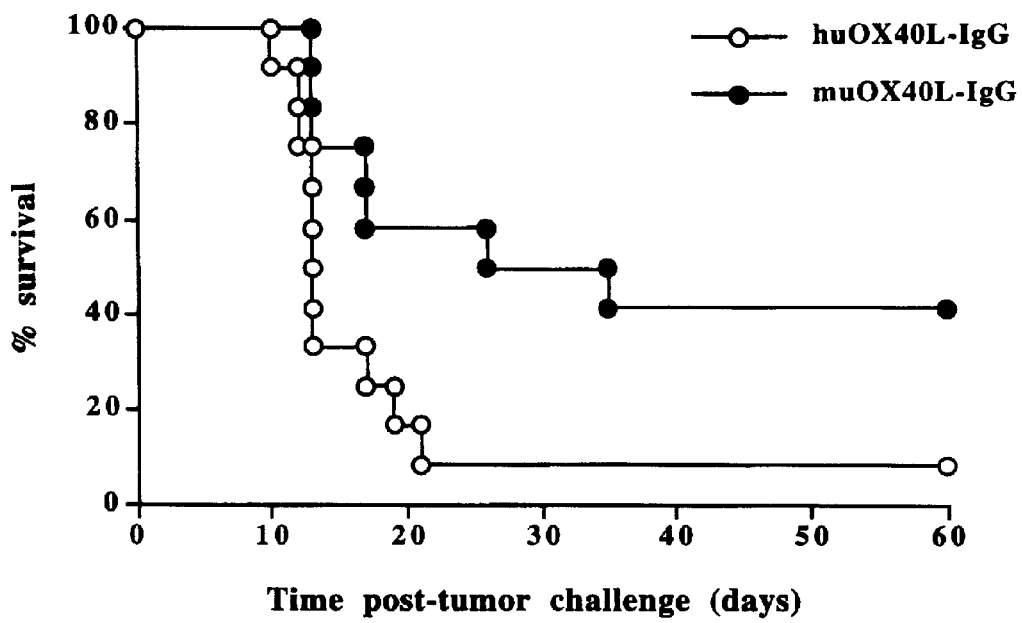
Figure 14B:
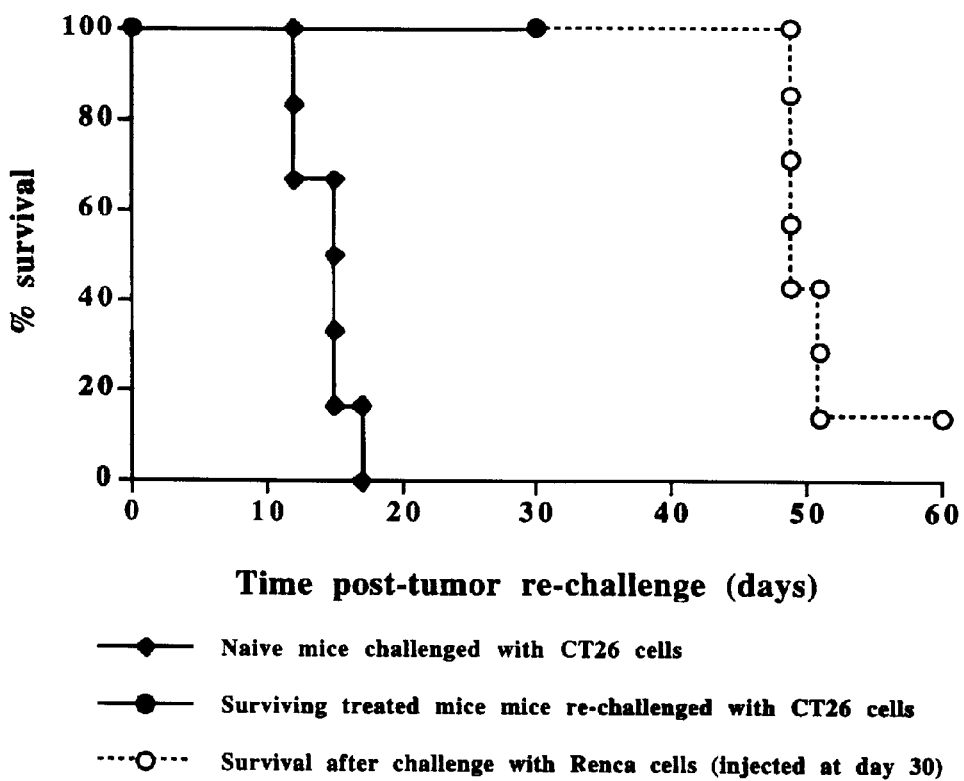

14A shows that multiple injection was beneficial to tumor-free survival with a p-value of higher confidence (p=0.01) than the two injection dose scheme. Seven of the surviving mice from the mOX-40L:Ig treated group were then rechallenged with CT26. FIG. 14B shows that all of the mOX40L:Ig mice resisted the challenge and remained tumor-free, while all the naive control mice succumbed to the tumor challenge. The 7 tumor-free mice were then rechallenged with a syngeneic tumor from a different tissue origin (Renca—renal origin) to test for a tumor-specific response. Six of 7 of the CT26 resistant mice had to be sacrificed due to tumor burden associated with the Renca tumor, which is believed to indicate that the CT26-resistant mice had specificity for tumor antigens associated with colon cancer.

Summary of Examples 6–9

OX-40R Engagement During Tumor Priming

Table I summarizes the data in four tumor models, examples 6–9, in which OX40R was engaged during tumor priming. The data suggest that the more immunogenic tumors respond to a greater degree to the therapy, but still a degree of therapeutic results was also seen in the poorly immunogenic melanoma model (F 10). Data for all the tumor lines have been shown in the previous figures except for the SM1 breast cancer line. The SM1 tumor cell line is weakly immunogenic (data not shown). Mice that have been injected with the SM1 tumor and subsequently OX40L:Ig on days 3 and 7 post-tumor inoculation had enhanced anti-tumor activity as shown by the increase of tumor-free survival. The SM1 data was subjected to log-rank statistical analysis and shown to be significant with a p value=0.01.

TABLE I

Examples 6–9: Summary of OX-40R Engagement During Tumor Priming

| Tumor Origin | Immuno-genicity | Treatment | Tumor Free/Injected Mice |
|---|---|---|---|
| MCA 303 (Sarcoma) | Moderate | mOX-40L:Ig | 9/16 |
|  |  | saline or DR3:Ig | 0/16 |
| CT26 (Colon Carcinoma) | Moderate | mOX-40L:Ig | 9/24 |
|  |  | hOX-40L:Ig | 2/24 |
| SM1 (Breast Cancer) | Weakly | mOX-40L:Ig | 7/28 |
|  |  | saline | 1/28 |
| B 16/FIO (Melanoma) | Poorly | mOX-40L:Ig | 5/20 |
|  |  | saline | 0/20 |
|  |  | antiOX-40R | 5/25 |
|  |  | rat Ig | 0/25 |

It is believed that engaging the OX-40R in vivo during tumor priming showed a significant therapeutic benefit in several tumor models. The effect was dose dependent and created long-lasting tumor-specific immunity in the mice that were cured from the initial tumor challenge. Other data showing that the OX-40R+ cells within the inflammatory lesions in EAE were the T cells that responded to autoantigen suggest that the experiments described here were targeting the tumor-Ag specific cells with the OX-40R-specific therapy. It has been shown that engaging OX-40R in vitro causes a potent costimulatory event that enhances T cell cytokine production, proliferation, and survival. Therefore engaging the OX40R during tumor priming is believed to be enhancing tumor-Ag specific CD4+ T cell expansion and function leading to tumor-free survival. The appearance of OX-40R+ T cells adjacent to tumor cells in breast cancer biopsies suggests that these findings can be applied in human clinical trials with similar therapeutic effects.

Engaging OX-40R in vivo during tumor priming led to a percentage of tumor-free mice in 4 different solid tumors eminating from for 4 separate tissue types. The data suggest that OX-40R based therapy can generally enhance the immune system, not only for tumor immunity, but also as an immunologic adjuvant for all vaccine types (viral, bacterial, etc.). OX-40R-specific immune enhancement has been described with a showing that an antibody to the OX-40R, delivered in vivo, could exacerbate autoimmune disease and convert a chronic form of GVHD to acute GVHD.

It is believed that huOX-40L:Ig fusion protein is an example of a protein applicable to the present invention that can be used in human clinical trials and can stimulate human T cells in vitro. Both the antibody and the soluble OX-40L fusion protein can work with similar potency in the tumor models mentioned here (FIG. 13 and other data not shown), but it is possible that the antibody may have some advantage in the future if it turns out to be less immunogenic and to have a longer-half life in vivo.

Enhancement of tumor immunity with antibodies such as anti-4-1 BB or anti-CTLA4 are other examples of T cell activation antigens which when triggered or blocked enhance tumor-specific immunity. Like the OX-40R, the 4-1 BB receptor was originally described as a T cell activation antigen that is a member of the TNF-receptor family and has potent costimulatory properties. The 4-1 BB receptor is expressed on CD8 and CD4 T cells as well as NK cells. The 4-1 BB receptor costimulatory function appears to be primarily effective on CD8+ T cells, and engagement of this receptor during tumor priming led to a 50-fold increase in tumor-specific CD8+ T cell cytolytic function and enhanced tumor-free survival. The CTLA-4 protein is expressed on both CD8 and CD4 T cells and when engaged by its ligand(s) (B7.1 or B7.2) induces a down-regulatory signal to the T cell. Antibodies that block CTLA-4/B7 interaction enhance Ag-specific T cell function and can ultimately enhance tumor specific immunity. The OX-40R specific therapy was potent on its own but has not yet led to 100% tumor-free mice, therefore therapy combining anti-CTLA4 or anti-4-1 BB with anti-OX-40R engagement according to the present invention may provide advantageous embodiments of the present invention, to accentuate Ag-specific T cell therapy. Alternative tumor-specific T cell therapies can combine two or more of these antibodies during tumor priming with the aim of enhancing both CD4 and CD8 Ag-specific effector/memory T cell responses.

In vivo engagement of the OX-40R during Ag-specific priming is believed to increase the number and life-span of Ag-specific CD4+ T cells (data not shown). Most T cells become susceptible to activated induced cell death (AICD) after encountering Ag at the effector T cell stage and only a few go on to become memory T cells. It is believed that engaging the OX-40R during tumor priming targets the tumor-reactive CD4+ T cells and spares them from AICD. Increasing numbers of Ag-specific cells allows the mice to stay tumor-free and fight a secondary tumor challenge. FIG. 11B shows that OX-40R treated tumor-immune mice can confer anti-tumor immunity through the adoptive transfer of CD8-depleted spleen cells. This data suggest that there is an increase and/or enhancement of tumor-Ag specific memory CD4+ T cells and they are able to transfer adoptive protection. CD4+ T cells may not be the ultimate effector cells that interact with the tumor because in all four models the tumor cells do not express MHC class II. Nevertheless enhanced cytokine production by tumor Ag-specific CD4+ T cells may be effective by helping to activate CD8+ T cells, NK cells, and macrophages which in turn can directly interact with and destroy tumors.

OX-40R is believed only to be expressed on CD4+ T cells isolated from the inflammatory site in cancer and autoimmune disease and is turned over quite rapidly (within 24–48 hr). However, it has been shown that both CD4 and CD8 T cells can express OX-40R if stimulated in vitro with Con A or PHA. It appears that the only way to upregulate OX-40R expression on T cells is through TCR engagement. Even in highly inflammatory situations, such as superAg stimulation, there appears to be no bystander upregulation of the OX-40R on Ag non-specific cells. In mice injected with the superantigen SEA, the OX-40R is only expressed on Vbeta3/CD4+ T cells which is the target TCR for this superAg. Therefore, it is believed that engaging the OX-40R during tumor priming in vivo targets the most recently Ag-activated T cells.

It has been shown that inflammation associated with superAg stimulation and clinical signs of EAE involves the production of Th1 cytokines. It is believed that engaging the OX-40R on Th1 lines can accentuate T cell proliferation by upregulating transcription and translation of IL-2, and that effector T cells appear to be more sensitive to OX-40R specific costimulation than naive T cells. Effector T cells that have been differentiated to produce either Th1 or Th2 cytokines are both sensitive to OX-40R-specific costimulation. Engaging the OX-40R on Th2 effector cells increased translation and secretion of IL-4 and IL-5 and enhanced their proliferation. Two reports recently showed that engaging the OX40R can polarize cells to the Th2 phenotype. Our data suggest that T cell polarization is dependent on the cytokine milieu that is surrounding the T cells during differentiation and engaging the OX-40R will accentuate both a Th1 or Th2 response. It has been shown that an anti-tumor Th2 immune response does not lead to tumor eradication, but a type 1 response does. Therefore, it is expected that it will be advantageous to enhance Th1 responses during tumor priming (with IL-12, IFN-gamma, and/or anti-IL-4) in order to get optimal anti-tumor immune response when administering reagents that engage the OX-40R in vivo.

OX40L is expressed only on activated antigen presenting cells such as B cells, dendritic cells, endothelial cells, and macrophages. In vivo expression of the OX-40L appears to occur in highly inflammatory situations such as infection of mice with MMTV (draining LN) or in mice with EAE on macrophages isolated from the inflamed organ (brain). Even in normal primary T cell responses such as immunization with Ag in CFA OX-40L expression was quite low on spleen macrophages. The OX-40R is expressed every time a T cell is triggered through the TCR, therefore the potent OX-40R costimulatory effects might be regulated by the inaccessibility of the OX40L on APC. The immune system has evolved to generate an immune response to clear foriegn entities rapidly, and then readily downregulate itself. Since OX-40L-mediated costimulation is quite potent at the effector T cell stage, it may only be neccessary in cases where a massive invasion occurs which in turn causes a long-lasting inflammation. Aggressive tumors downregulate immune responses through immunosupressive mechanisms, therefore the APC near the tumor site probably do not express the OX40L. It is believed that tumor-specific immune responses were being enhanced in the experiments described above by adding a signal that engages the OX-40R in vivo and therefore a percentage of the tumor challenged mice were able to remain tumor-free.

In summary, in Examples 6–9 above, engaging the OX-40R during tumor priming is believed to have been effective to delay and prevent the appearance of tumors as compared to control treated mice. The OX-40R effect was dose dependent and was observed in a variety of immunogenic and non-immunogenic tumor models. OX40R expression was found on T cells localized at the tumor site in several different human cancers (melanoma, head and neck, and breast cancer (see e.g. FIG. 9)). Examination of the physical relationship of the OX-40R+ T cells to breast cancer cells in both a 1° tumor and a tumor invaded lymph node indicated that the OX-40R+ T cells were concentrated in areas surrounding the tumor and it is believed that they are tumor-specific T cells. The combination of the OX-40R therapeutic data in the mouse tumor model and the appearance of OX-40R+ in tumor bearing patients is believed to indicate immune tumor-reactivity can be enhanced with reagents designed engage the OX-40R in patients with cancer. The data are believed to indicate that engaging OX-40R especially for example during Ag-specific priming can be a useful adjuvant in a wide variety of vaccine settings.

The foregoing examples further illustrate the present invention, but are not limiting. Numerous variations and modifications can be made in the methods and compositions disclosed herein, and such variations and modifications are encompassed within the invention. The present disclosure also extends to combinations and subcombinations of the features mentioned and described herein. The documents referred to are hereby incorporated by reference in their entirety for all purposes.

REFERENCES

Better et al. (1989) *Methods in Enzymology* 178: 476–496.
Better and Horowitz (1990) Advances in Gene Technology: The Molecular Biology of Immune Disease & the Immune Response (ICSU Short Reports), (Streilein et al., eds.) vol. 10:105.
Calderhead et al. (1993) *J. Immunol.* 151: 5261–5271.
Dubey et al. (1995) *J. Immunol.* 155: 45.
Glockshuber et al. (1990) *Biochemistry* 29: 1362–1367.
Godfrey et al. (1994) *J. Exp. Med.* 180: 757–762.
Harlow and Lane (1988) Antibodies, A Laboratory Manual, Cold Spring Harbor Laboratory (ISBN 0-87969-314-2).
Huntzicker et al. (1995) *9th International Congress of Immunology,* San Francisco, Abstract #5170:872.
Kaye and Hedrick (1989) *Nature* 341:746
Krummel et al. (1996) *J. Exp. Med.* 183: 2533.
Latza et al. (1994) *Eur. J. Immunol.* 24: 677–683.
Lenschow et al. (1996) *Ann. Rev. Immunol.* 14: 233.
Mallett et al. (1990) *EMBO J.* 9: 1063–1068.
Miura et al. (1991) *Mol. Cell. Biol.* 11: 1313–1325.
Paterson et al. (1987) *Mol. Immunol.* 24: 1281–1290.
Sambrook et al. (1989). In *Molecular Cloning: A Laboratory Manual,* Cold Spring Harbor, N.Y.
Vandenbark et al. (1985) *J. Immunol.* 135: 223.
Vetto et al. (1997) *Am. J. Surg.* 174: 258–265.
Walunas et al. (1996) *J. Exp. Med.* 183: 2541–2550.
Weinberg et al. (1996) *Nature Medicine* 2: 183–189.
Weinberg et al. (1994) *J. Immunol.* 152: 4712–4721.

What is claimed is:

1. A method of enhancing an immune response to an antigen in a mammal, comprising administering to the mammal a composition comprising a purified OX-40 receptor binding agent and a pharmaceutically acceptable carrier; wherein said OX-40 receptor binding agent is selected from the group consisting of OX-40L, soluble OX-40L, a fusion protein comprising OX-40L, and a fusion protein comprising an OX-40L extracellular domain or an active fragment thereof; and wherein said composition is administered to the mammal such that the OX-40 receptor binding agent is presented to T cells of the mammal during or shortly after priming of the T cells by the antigen, thereby enhancing the immune response.

2. The method according to claim 1 wherein the composition is administered to the mammal about 3 to 7 days after priming.

3. The method according to claim 1 wherein the purified OX-40 receptor binding agent is OX-40L.

4. The method according to claim 1 wherein the purified OX-40 receptor binding agent is soluble OX-40L.

5. The method according to claim 1 wherein the fusion protein comprises OX-40L covalently linked to a second protein domain.

6. The method according to claim 1 wherein the fusion protein comprises the OX-40L extracellular domain or active fragment thereof covalently linked to a second protein domain.

7. The method of claim 5 or 6 wherein the second protein domain is an immunoglobulin constant domain.

8. The method of claim 7 wherein the immunoglobulin constant domain is a human immunoglobulin constant domain.

9. The method according to claim 1 wherein the antigen is selected from the group consisting of a viral antigen, a bacterial antigen and a tumor antigen.

10. A method for stimulating an immune response to a tumor cell in a mammal, comprising administering to the mammal a therapeutically effective dose of a composition comprising a purified OX-40 receptor binding agent and a pharmaceutically acceptable carrier; wherein said OX-40 receptor binding agent is selected from the group consisting of OX-40L, soluble OX-40L, a fusion protein comprising OX-40L, and a fusion protein comprising an OX-40L extracellular domain or an active fragment thereof, thereby stimulating the immune response.

11. The method according to claim 10 wherein the purified OX-40 receptor binding agent is OX-40L.

12. The method according to claim 10 wherein the purified OX-40 receptor binding agent is soluble OX-40L.

13. The method according to claim 10 wherein the fusion protein comprises OX-40L covalently linked to a second protein domain.

14. The method according to claim 10 wherein the fusion protein comprises the OX-40L extracellular domain or active fragment thereof covalently linked to a second protein domain.

15. The method of claim 13 or 14 wherein the second protein domain is an immunoglobulin constant domain.

16. The method of claim 15 wherein the immunoglobulin constant domain is a human immunoglobulin constant domain.

17. A method of enhancing an immune response against a tumor in a mammal, comprising administering directly to the tumor site a composition comprising a purified OX-40 receptor binding agent and a pharmaceutically acceptable carrier; wherein said OX-40 receptor binding agent is selected from the group consisting of OX-40L, soluble OX-40L, a fusion protein comprising OX-40L, and a fusion protein comprising an OX-40L extracellular domain or an active fragment thereof, thereby enhancing the immune response.

18. The method according to claim 17 wherein the purified OX-40 receptor binding agent is OX-40L.

19. The method according to claim 12 wherein the purified OX-40 receptor binding agent is soluble OX-40L.

20. The method according to claim 17 wherein the fusion protein comprises OX-40L covalently linked to a second protein domain.

21. The method according to claim 17 wherein the fusion protein comprises the OX-40L extracellular domain or active fragment thereof covalently linked to a second protein domain.

22. The method of claim 20 or 21 wherein the second protein domain is an immunoglobulin constant domain.

23. The method of claim 22 wherein the immunoglobulin constant domain is a human immunoglobulin constant domain.

* * * * *